United States Patent [19]
Katz et al.

[11] Patent Number: 5,976,794
[45] Date of Patent: *Nov. 2, 1999

[54] METHOD FOR MOLECULAR STAGING OF PROSTATE CANCER

[75] Inventors: Aaron E. Katz, Armonk; Ralph Buttyan; Anthony Raffo, both of New York; Carl A. Olsson, Larchmont, all of N.Y.

[73] Assignee: The Trustees of Columbia University in the City of New York, New York, N.Y.

[ * ] Notice: This patent is subject to a terminal disclaimer.

[21] Appl. No.: 08/718,547

[22] PCT Filed: Apr. 14, 1995

[86] PCT No.: PCT/US95/04680

§ 371 Date: Jan. 13, 1997

§ 102(e) Date: Jan. 13, 1997

[87] PCT Pub. No.: WO95/28498

PCT Pub. Date: Oct. 26, 1995

Related U.S. Application Data

[63] Continuation-in-part of application No. 08/229,391, Apr. 15, 1994, abandoned.

[51] Int. Cl.[6] .............................. C12Q 1/68; C12P 19/34; C07H 21/04
[52] U.S. Cl. ........................... 435/6; 435/91.2; 435/91.5; 435/91.51; 536/24.31; 536/24.33
[58] Field of Search .............................. 135/6, 91.2, 91.5, 135/91.51; 536/24.31, 24.33; 436/63, 64, 164, 172; 935/8, 16, 17, 78

[56] References Cited

U.S. PATENT DOCUMENTS

| | | | |
|---|---|---|---|
| 5,437,978 | 8/1995 | Wbakata | 435/6 |
| 5,506,106 | 4/1996 | Croce et al. | 435/6 |

FOREIGN PATENT DOCUMENTS

| | | |
|---|---|---|
| 0520794A1 | 12/1992 | European Pat. Off. . |
| WO 94/10343 | 5/1994 | WIPO . |

OTHER PUBLICATIONS

Young et al. Cancer Research (1991) 51:3748–3752.

Anscher, M.S. and Pronsnitz, L.R. (1987) "Postoperative radiotherapy for patients with carcinoma of the prostate undergoing radical prostatectomy with positive surgical margins, seminal vesicle involvement and/or penetration through the capsule." J Urol 138, 1407–1412.

Batson, O.V. (1940) "The function of the vertebral veins and their role in the spread of metastasis." Ann Surg 112, 138–142.

Benson, M.C., et al. (1992) "Prostate Specific Antigen Density: A means of distinguishing benign prostatic hypertrophy and prostate cancer." J Urol 147, 815–816.

(List continued on next page.)

*Primary Examiner*—Carla J. Myers
*Attorney, Agent, or Firm*—John P. White; Cooper & Dunham LLP

[57] ABSTRACT

A method for enhancing the detection of prostate specific antigen in a biological sample comprising (a) extracting mRNA from the sample: (b) contacting the mRNA from step (a) with reverse transcriptase under conditions allowing for the production of cDNA; (c) contacting the cDNA from step (b) with a pair of reverse transcriptase polymerase chain reaction primers capable of specifically hybridizing with DNA encoding prostate specific antigen wherein one such primer is an oligonucleotide of 12 to 30 nucleotides in length and comprises the sequence 5-CACCCATCCTA-3' and wherein the second such primer is an oligonucleotide of 12 to 30 nucleotides in length and comprises the sequence 5'-TCCAGCCACGAC-3'; and wherein at least one of the primers is covalently linked to a modified digoxigenin molecule and under conditions allowing for extension of the primers; and (d) detecting the resulting amplified DNA.

36 Claims, 10 Drawing Sheets

OTHER PUBLICATIONS

Catalona, W.J., et al. (1985) "Nerve–sparing radical protatectomy: Extraprostatic tumor extension and preservation of erectile function." J Urol 134, 1149–1151.

Chiarodo, A. (1991) "National Cancer Institute Round Table on prostate cancer." Cancer Res 51, 2498–2505.

Deguchi, T., et al. (1993) "Detection of micrometastatic prostate cancer cells in lymph nodes by reverse transcriptase–polymerase chain reaction." Cancer Res 53, 5350–5354.

Digby, M., et al. (1989) "Human prostate specific antigen (PSA) genes: structure and linkage to the kallikrein–like gene, hGK–1." Nucl Acids Res 17, 2137.

Dobbs, P.R., et al. (1981) "The role of the vertebral veins in the dissemination of prostate cancer." J Urol 126, 753–755.

Epstein, J., et al. (1993) "Correlation of pathologic findings after radical retropubic prostatectomy." Cancer 71, 3582–3593.

Fiss, E.H. (1992) "Reverse Blot hybridization for dection and identification of microbacteria to the species level in the clinical laboratory." J Clinical Res 30, 1220–1224.

Gerber, G.S., et al. (1992) "Local staging of prostate cancer by tumor volume, prostate–specific antigen, and transrectal ultrasound." Urology 40, 311–316.

Hamby, F.C., et al. (1979) "Circulating prostate specific antigen–positive cells correlate with metastatic prostate cancer." Brit J Urol 69, 392–396.

Holmstrom, K. (1993) "A highly sensitive and fast nnradioactive method for dection of polymerase chain reaction products." Analytical Biochem 209, 278–283.

Horoszewicz, J.S., et al. (1983) "LNCap model of human prostatic carcinoma." Can Res 43, 1809–1817.

Hricak, H., et al. (1987) "Prostatic carcinoma: Staging by clinical assessment, CT, and MR imaging." Radiology 162, 331–336.

Hudson, M.A., et al. (1989) "Clinical use of prostate specific antigen density in patients with prostate cancer." J Urol 142, 1011–1017.

Klobeck, H.G., et al. (1989) Genomic sequences of human prostate specific antigen (PSA). Nucleic Acids Res 17, 3981.

Lanzillo, J.J. (1990) "Preparation of digoxigenin–labeled probes by the polymerase chain reaction." Biotech 8, 620–622.

Moreno, J.G., et al. (1992) "Detection of hematogenous micrometastasis in patients with prostate cancer." Can Res 52, 6110–6112.

Mukamel, E., et al. (1982) "Pitfalls in preoperative staging in prostate cancer." Urol 30, 318–321.

Oesterling, J., et al. (1983) "The use of prostate–specific antigen in staging patients with newly diagnosed prostate cancer." JAMA 269, 57–60.

Platt, J.F., et al. (1987) "The accuracy of CT in the staging of the prostate." Amer J Roent 149, 315–318.

Seaman, E., et al. (1993) "The use of PSAD to predict D–O prostatic carcinoma." J Urol 149, 300A.

Wang, M.C., et al. (1979) "Purification of a human prostate specific antigen." Invest URol 17, 159–163.

Winter, H.I., et al. (1991) "Preoperative prostate–specific antigen in prediction pathological stage and grade after radical prostatectomy." Urology 38, 202–205.

Anonymous (1994) In: Boehringer Mannheim Catalog, p. 61.

Hermanek et al. (1995) In: Oxford Textbook of Oncology, vol. 1, Oxford University Press, New York, pp. 880–887.

Katz et al. (Dec. 1993) Molecular staging of prostate cancer with the use of an enhanced reverse transcriptase–PCR assay, Urol Res 21, 462 (abstract 082).

Kawasaki et al. (1989) In: PCR protocols: a guide to methods and applications, Innis et al., Eds., Academic Press, New York, pp. 21–27.

Katz et al. (1994) Molecular staging of prostate cancer with the use of an enhanced reverse transcriptase–PCR assay Urology 43, 765–775 (Exhibit 3).

Lu–Yao et al. (1993) An assessment of radical prostatectomy: time trends, geographic variation and outcomes, JAMA 269, 2633–2655 (Exhibit 4).

Mettlin and Murphy (1994) The national cancer data base report on prostate cancer, Cancer 74, 1604–1608 (Exhibit 5).

Smith et al. (1991) Dectection of melanoma cells in peripheral blood by means of reverse transcriptase polymerase chain reaction, The Lancet 338, 1227–1229 (Exhibit 6).

Voges et al. (1992) Morphologic analysis of surgical margins with positive findings in prostatectomy for adenocarcinoma of the prostate, Cancer 69, 520–526 (Exhibit 7).

Ethidium Bromide Detection

Enhanced Detection

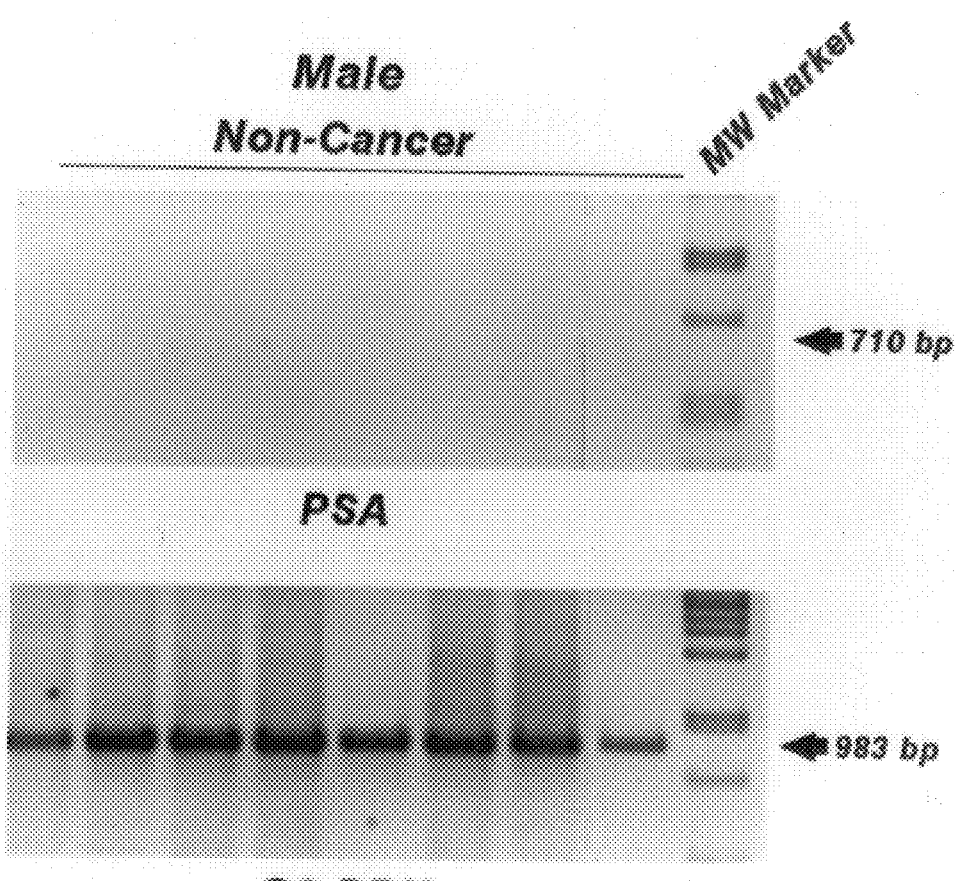

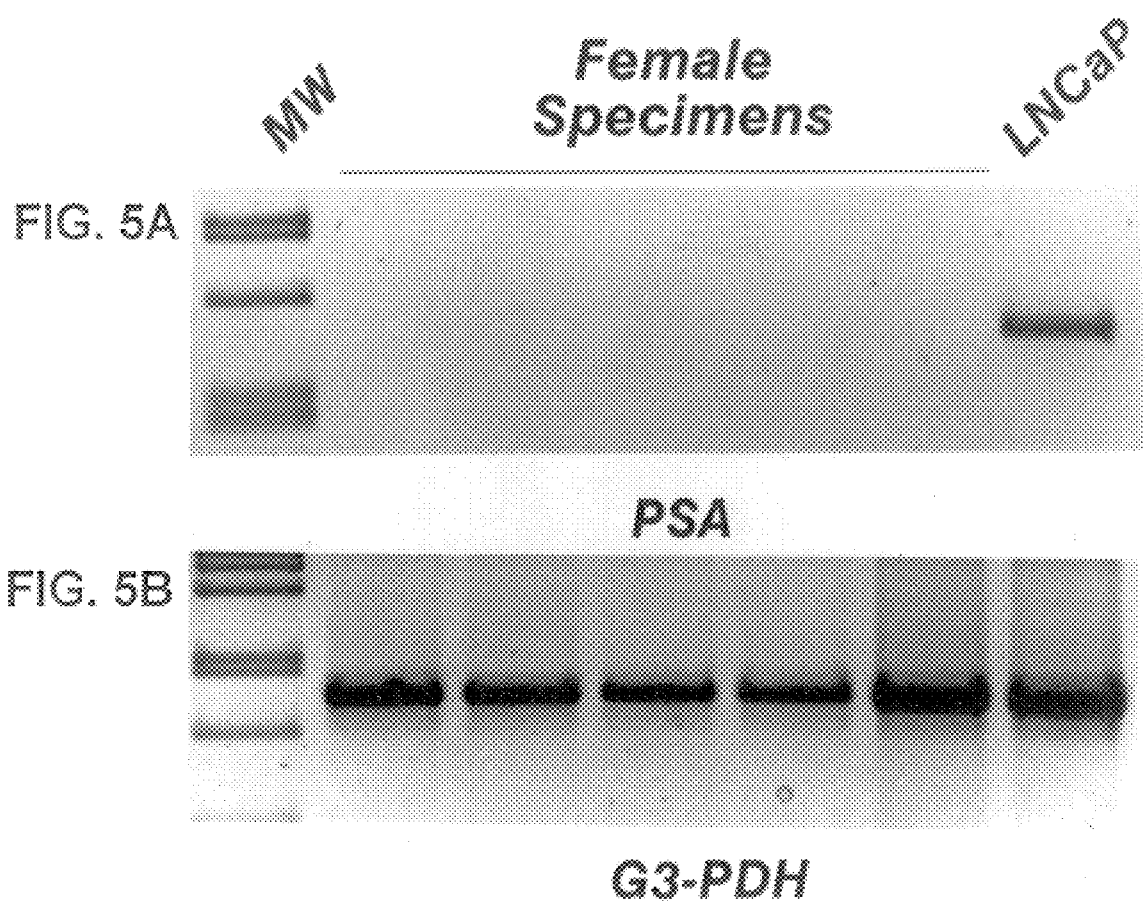

FIG. 6A

| | | | | |
|---|---|---|---|---|
| AAGTTCCCT | TCTCCCAGTC | CAAGACCCCA | AATCACCACA | AAGGACCCAA | TCCCCAGACT | 60
| CAAGATATGG | TCTGGGCGCT | GTCTTGTGTC | TCCTACCCTG | ATCCCTGGGT | TCAACTCTGC | 120
| TCCCAGAGCA | TGAAGCCTCT | CCACCAGCAC | CAGCCACCAA | CCTGCAAACC | TAGGGAAGAT | 180
| TGACAGAATT | CCCAGCCTTT | CCCAGCTCCC | CCTGCCCATG | TCCCAGGACT | CCCAGCCTTG | 240

FIG. 6B

```
GTTCTCTGCC CCCGTGTCTT TTCAAACCCA CATCCTAAAT CCATCTCCTA TCCGAGTCCC    300
CCAGTTCCTC CTGTCAACCC TGATTCCCCT GATCTAGCAC CCCCCTGCA GGTGCTGCAC    360
CCCTCATCCT GTCTCGG ATT GTG GGA GGC TGG GAG TGC GAG AAG CAT TCC      410
                   Ile Val Gly Gly Trp Glu Cys Glu Lys His Ser
                    1               5                   10

CAA CCC TGG CAG GTG CTT GTA GCC TCT CGT GGC AGG GCA GTC TGC GGC    458
Gln Pro Trp Gln Val Leu Val Ala Ser Arg Gly Arg Ala Val Cys Gly
             15                  20                  25

GGT GTT CTG GTG CAC CCC CAG TGG GTC CTC ACA GCT ACC CAC TGC ATC    506
Gly Val Leu Val His Pro Gln Trp Val Leu Thr Ala Thr His Cys Ile
         30                  35                  40

AGG AAC AAA AGC GTG ATC TTG CTG GGT CGG CAC AGC AGC CTG TTT CAT CCT    554
Arg Asn Lys Ser Val Ile Leu Leu Gly Arg His Ser Ser Leu Phe His Pro
     45                  50                  55

GAA GAC ACA GGC CAG GTA TTT CAG GTC AGC CAC AGC TTC CCA CAC CCG    602
Glu Asp Thr Gly Gln Val Phe Gln Val Ser His Ser Phe Pro His Pro
 60                  65                  70                  75
```

FIG. 6C

```
CTC TAC GAT ATG AGC CTC CTG AAG AAT CGA TTC CTC AGG CCA GGT GAT    650
Leu Tyr Asp Met Ser Leu Leu Lys Asn Arg Phe Leu Arg Pro Gly Asp
            80                    85                    90

GAC TCC AGC CAC GAC CTC ATG CTG CTC CGC CTG TCA GAG CCT GCC GAG    698
Asp Ser Ser His Asp Leu Met Leu Leu Arg Leu Ser Glu Pro Ala Glu
        95                   100                   105

CTC ACG GAT GCT ATG AAG GTC ATG GAC CTG CCC ACC CAG GAG CCA GCA    746
Leu Thr Asp Ala Met Lys Val Met Asp Leu Pro Thr Gln Glu Pro Ala
    110                   115                   120

CTG GGG ACC ACC TGC TAC GCC TCA GGC TGG GGC AGC ATT GAA CCA GAG    794
Leu Gly Thr Thr Cys Tyr Ala Ser Gly Trp Gly Ser Ile Glu Pro Glu
125                   130                   135

GAG TTC TTG ACC CCA AAG AAA CTT CAG TGT GTG GAC CTC CAT GTT ATT    842
Glu Phe Leu Thr Pro Lys Lys Leu Gln Cys Val Asp Leu His Val Ile
140                   145                   150                   155
```

FIG. 6D

| TCC | AAT | GAC | GTG | TGT | GCG | CAA | GTT | CAC | CCT | CAG | AAG | GTG | ACC | AAG | TTC | 890 |
| Ser | Asn | Asp | Val | Cys | Ala | Gln | Val | His | Pro | Gln | Lys | Val | Thr | Lys | Phe | |
| | | 160 | | | | | | 165 | | | | | | 170 | | |

| ATG | TGT | GCT | GGA | CGC | TGG | ACA | GGG | GGC | AAA | AGC | ACC | TGC | TCG | GGT | | 938 |
| Met | Leu | Cys | Ala | Gly | Arg | Trp | Thr | Gly | Gly | Lys | Ser | Thr | Cys | Ser | Gly | |
| | | 175 | | | | | | 180 | | | | | | 185 | | |

| GAT | TCT | GGG | GGC | CCA | CTT | GTC | TGT | AAT | GGT | GTG | CTT | CAA | GGT | ATC | ACG | 986 |
| Asp | Ser | Gly | Gly | Pro | Leu | Val | Cys | Asn | Gly | Val | Leu | Gln | Gly | Ile | Thr | |
| | | 190 | | | | | | 195 | | | | | | 200 | | |

| TCA | TGG | GGC | AGT | GAA | CCA | TGT | GCC | CTG | CCC | GAA | AGG | CCT | TCC | CTG | TAC | 1034 |
| Ser | Trp | Gly | Ser | Glu | Pro | Cys | Ala | Leu | Pro | Glu | Arg | Pro | Ser | Leu | Tyr | |
| | 205 | | | | | | 210 | | | | | | 215 | | | |

| ACC | AAG | GTG | GTG | CAT | TAC | CGG | AAG | TGG | ATC | AAG | GAC | ACC | ATC | GTG | GCC | 1082 |
| Thr | Lys | Val | Val | His | Tyr | Arg | Lys | Trp | Ile | Lys | Asp | Thr | Ile | Val | Ala | |
| 220 | | | | | | 225 | | | | | 230 | | | | 235 | |

| AAC | CCC | TGAGCACCCC | TATCAACTCC | CTATTGTAGT | AAACTTGGAA | CCTTGAAAT | | | | | | | | | | 1138 |
| Asn | Pro | | | | | | | | | | | | | | | |

GACCAGGCCA AGACTCAGGC CTCCCCAGTT CTACTGACCT TTGTCCTTAG GTGTGAGGTC    1198

FIG. 6E

```
CAGGGTTGCT AGGAAAAGAA ATCAGCAGAC ACAGGTGTAG ACCAGAGTGT TTCTTAAATG   1258

GTGTAATTTT GTCCTCTCTG TGTCCTGGGG AATACTGGCC ATGCCTGGAG ACATATCACT   1318

CAATTCTCT GAGGACACAG ATAGGATGGG GTGTCTGTGT TATTTGTGGG GTACAGAGAT    1378

GAAAGAGGGG TGGGATCCAC ACTGAGAGAG TGGAGAGTGA CATGTGCTGG ACACTGTCCA   1438

TGAAGCACTG AGCAGAAGCT GGAGGCACAA CGCACCAGAC ACTCACAGCA AGGATGGAGC   1498

TGAAAACATA ACCCACTCTG TCCTGGAGGC ACTGGGAAGC CTAGAGAAGG CTGTGAACCA   1558

AGGAGGGAGG GTCTTCCTTT GGCATGGGAT GGGGATGAAG TAAGGAGAGG GACTGACCCC   1618

CTGGAAGCTG ATTCACTATG GGGGGAGGTG TATTGAAGTC CTCCAGACAA CCCTCAGATT   1678

TGATGATTTC CTAGTAGAAC TCACAGAAAT AAAGAGCTGT TATACTGTGA A            1729
```

METHOD FOR MOLECULAR STAGING OF PROSTATE CANCER

This application is a continuation in part of U.S. Ser. No. 08/229,391, filed Apr. 15, 1994, which is now abandoned and the contents of which are hereby incorporated by reference.

This invention was made with support under Grant No. CA58089 from the National Cancer Institute, U.S. Department of Health and Human Services. Accordingly, the U.S. Government has certain rights in the invention.

BACKGROUND OF THE INVENTION

Throughout this application, various publications are referenced. Full citations for these references may be found at the end of the specification immediately preceding the claims. The disclosure of these publications is hereby incorporated by reference into this application to describe more fully the art to which this invention pertains.

Approximately 60% of newly diagnosed patients with prostate cancer will have established metastasis at the time of diagnosis (2). Once the disease has spread to distant rites, the overall prognosis is poor (3,4). Organ-confined prostate cancer should be curative upon removal of the gland, however screening modalities to assess early metastases often fail to identify a significant subset of patients with locally invasive disease (involving penetration of the capsule or seminal vesicle). Recent studies report that up to 40–50% of patients who were thought to have clinically localized disease were found to be understaged subsequent to radical surgery (5,6,7). This failure rate creates a clinical dilemma since operative therapy is not the appropriate treatment modality for these patients. Clearly, development of a more sensitive means to identify patients with micrometastic, locally invasive disease is warranted.

Prostate cancer metastases are more frequently found in the pelvic lymph nodes and on bone and these are sites surveyed most aggressively in patients diagnosed with prostate cancer. The involvement of draining lymph nodes in the dissemination of this cancer is expected, given our understanding of solid tumor behavior. The means by which the prostate cancer cells target the bone is debated, but suspected to involve blood vessels to the lower spine, specifically the vertebral venous plexus (8,9). This spread presupposes that prostate cancer cells are shed into the blood stream and implies a role for hematogenous dissemination in prostate cancer progression.

Indeed, a preliminary study showing that prostate cells can be putatively identified in blood specimens of patients with metastatic prostate cancer supports the concept of blood-borne metastasis (10).

This previous study reported that cells synthesizing prostate specific antigen (PSA) were present in the circulating blood of patients with prostate specific antigen (PSA) were present in the circulating blood of patients with prostate cancer metastases. Since the expression of this protein is restricted to epithelial cells of the prostate gland, the detection of PSA synthesizing cells in the circulation indicates an unexpected and potentially abnormal situation. Here, we describe our development of an extremely sensitive "enhanced" PCR-based assay that allows us to identify PSA-synthesizing cells even when they are highly diluted in a population of peripheral lymphocytes. When this assay was applied to RNA extracted from peripheral blood cells of prostate cancer patients, it enabled us to distinguish the overwhelming majority of patients with overt metastatic disease as well as patients with locally invasive tumors that were understaged by conventional screening modalities (i.e. digital rectal exam, CT-scan and/or endorectal MRI). The remarkable accuracy of this assay in upstaging patients with apparent clinically localized disease could eliminate a significant number of prostate cancer patients from unnecessary operations and potentially increase the cure rate in patients who are treated by radical prostatectomy. Since this simple assay involves the molecular detection of a prostate-specific gene product, it represents the first reported instance of molecular staging of a solid human tumor.

SUMMARY OF THE INVENTION

The subject method provides a method for enhancing the detection of prostate specific antigen in a biological sample suspected of containing prostate specific antigen which comprises:

(a) extracting mRNA from the sample;

(b) contacting the mRNA from step (a) with reverse transcriptase under conditions allowing for the production of cDNA;

(c) contacting the cDNA from step (b) with a pair of reverse transcriptase polymerase chain reaction oligonucleotide primers capable of specifically hybridizing with DNA encoding prostate specific antigen, wherein one such primer is an oligonucleotide 12 to 30 nucleotides in length and having the sequence 5'-X-CACCCCATCCTA-Y-3' and the second such primer is an oligonucleotide 12 to 30 nucleotides in length and having the nucleotide sequence 5'-X'-TCCAGCCACGAC-Y'-3' wherein each of X, X', Y, and Y' may be present or absent, but if present X is A, GA, AGA, CAGA, ACAGA, CACAGA, ACACAGA, AACACAGA, TAACACAGA, ATAACACAGA, AATAACACAGA, AAATAACACAGA, or CAAATAACACAGA; X' is C, AC, GAC, TGAC, ATGAC, GATGAC, TGATGAC, GTGATGAC, GGTGATGAC, AGGTGATGAC or CAGGTGATGAC; Y is T, TC, TCT, TCTG, TCTGT, or TCTGTG; and Y' is C, CT, CTC, CTCA, CTCAT, CTCATG, or CTCATGC; and wherein at least one of the primers is covalently linked to a suitably modified digoxigenin molecule, under conditions allowing for hybridization of both primers to any cDNA encoding prostate specific antigen so as to obtain a double stranded duplex comprising the cDNA hybridized to the primers;

(d) contacting the double stranded duplex from step (c) with DNA polymerase under conditions allowing for the extension of the primers to produce cDNA encoding prostate specific antigen and comprising a suitably modified digoxigenin molecule; and (e) detecting the suitably modified digoxigenin molecule from the cDNA from step (d) thereby detecting prostate specific antigen.

The subject invention also provides a method for detecting prostate specific antigen in a biological sample suspected of containing prostate specific antigen which comprises:

(a) extracting mRNA from the sample;

(b) contacting the mRNA from step (a) with reverse transcriptase under conditions allowing for the production of cDNA;

(c) contacting the cDNA from step (b) with a pair of reverse transcriptase polymerase chain reaction oligonucleotide primers capable of specifically hybridizing with DNA encoding prostate specific antigen, wherein one such primer is an oligonucleotide 12 to 30 nucleotides in length and having the sequence 5'-X-CACCCCATCCTA-Y-3' and the second such primer is an oligonucleotide 12 to 30 nucleotides in length and having the nucleotide sequence 5'-X'-TCCAGCCACGAC-Y'-3' wherein each of X, X', Y, and Y' may be present or absent, but if present X is A, GA, AGA, CAGA, ACAGA, CACAGA, ACACAGA, AACACAGA, TAACACAGA, ATAACACAGA, AATAACACAGA, AAATAACACAGA, or CAAATAACACAGA; X' is C, AC, GAC, TGAC, ATGAC, GATGAC, TGATGAC, GTGATGAC, GGTGATGAC, AGGTGATGAC or CAGGTGATGAC; Y is T, TC, TCT, TCTG, TCTGT, or TCTGTG; and Y' is C, CT, CTC, CTCA, CTCAT, CTCATG, or CTCATGC; under conditions allowing for hybridization of both primers to any cDNA encoding prostate specific antigen so as to obtain a double stranded duplex comprising the cDNA hybridized to the primers;

(d) contacting the double stranded duplex from step (c) with DNA polymerase under conditions allowing for the extension of the primers to produce cDNA encoding prostate specific antigen; and (e) detecting the cDNA from step (d) thereby detecting prostate specific antigen.

The subject invention also provides a method of diagnosing prostate cancer in a subject which comprises:

(a) obtaining a biological sample from the subject;

(b) extracting mRNA from the sample;

(c) contacting the mRNA from (b) with reverse transcriptase under conditions allowing for the production of cDNA;

(d) contacting the cDNA from step (c) with a pair of reverse transcriptase polymerase chain reaction oligonucleotide primers capable of specifically hybridizing with DNA encoding prostate specific antigen, wherein one such primer is an oligonucleotide 12 to 30 nucleotides in length and having the sequence 5'-X-CACCCCATCCTA-Y-3' and the second such primer is an oligonucleotide 12 to 30 nucleotides in length and having the nucleotide sequence 5'-X'-TCCAGCCACGAC-Y' -3' wherein each of X, X', Y, and Y' may be present or absent, but if present X is A, GA, AGA, CAGA, ACAGA, CACAGA, ACACAGA, AACACAGA, TAACACAGA, ATAACACAGA, AATAACACAGA, AAATAACACAGA, or CAAATAACACAGA; X' is C, AC, GAC, TGAC, ATGAC, GATGAC, TGATGAC, GTGATGAC, GGTGATGAC, AGGTGATGAC or CAGGTGATGAC; Y is T, TC, TCT, TCTG, TCTGT, or TCTGTG; and Y' is C, CT, CTC, CTCA, CTCAT, CTCATG, or CTCATGC; under conditions allowing for hybridization of both primers to any cDNA encoding prostate specific antigen so as to obtain a double stranded duplex comprising the cDNA hybridized to the primers;

(e) contacting the double stranded duplex from step (d) with DNA polymerase under conditions allowing for the extension of the primers to produce cDNA encoding prostate specific antigen; and (f) detecting the cDNA from step (e) thereby diagnosing prostate cancer in the subject.

The subject invention further provides a method of determining the stage of prostate cancer in a subject which comprises:

(a) obtaining a biological sample from the subject;

(b) extracting mRNA from the sample;

(c) contacting the mRNA from (b) with reverse transcriptase under conditions allowing for the production of cDNA;

(d) contacting the cDNA from step (c) with a pair of reverse transcriptase polymerase chain reaction oligonucleotide primers capable of specifically hybridizing with DNA encoding prostate specific antigen, wherein one such primer is an oligonucleotide 12 to 30 nucleotides in length and having the sequence 5'-X-CACCCCATCCTA-Y-3' and the second such primer is an oligonucleotide 12 to 30 nucleotides in length and having the nucleotide sequence 5'-X' -TCCAGCCACGAC-Y' -3' wherein each of X, X', Y, and Y' may be present or absent, but if present X is A, GA, AGA, CAGA, ACAGA, CACAGA, ACACAGA, AACACAGA, TAACACAGA, ATAACACAGA, AATAACACAGA, AAATAACACAGA, or CAAATAACACAGA; X' is C, AC, GAC, TGAC, ATGAC, GATGAC, TGATGAC, GTGATGAC, GGTGATGAC, AGGTGATGAC or CAGGTGATGAC; Y is T, TC, TCT, TCTG, TCTGT, or TCTGTG; and Y' is C, CT, CTC, CTCA, CTCAT, CTCATG, or CTCATGC; under conditions allowing for hybridization of both primers to any cDNA encoding prostate specific antigen so as to obtain a double stranded duplex comprising the cDNA hybridized to the primers;

(e) contacting the double stranded duplex from step (d) with DNA polymerase under conditions allowing for the extension of the primers to produce cDNA encoding prostate specific antigen; and (f) detecting the cDNA from step (e) thereby determining the stage of prostate cancer in the subject.

The subject invention further provides an oligonucleotide 12 to 30 nucleotides in length and having the sequence 5'-X-CACCCCATCCTA-Y-3' wherein each of X and Y may be present or absent, but if present X is A, GA, AGA, CAGA, ACAGA, CACAGA, ACACAGA, AACACAGA, TAACACAGA, ATAACACAGA, AATAACACAGA, AAATAACACAGA, or CAAATAACACAGA; and Y is T, TC, TCT, TCTG, TCTGT, or TCTGTG.

The subject invention also provides an oligonucleotide 12 to 30 nucleotides in length and having the nucleotide sequence 5'-X'-TCCAGCCACGAC-Y'-3' wherein each of X' and Y' may be present or absent, but if present X' is C, AC, GAC, TGAC, ATGAC, GATGAC, TGATGAC, GTGATGAC, GGTGATGAC, AGGTGATGAC or CAGGTGATGAC; and Y' is C, CT, CTC, CTCA, CTCAT, CTCATG, or CTCATGC.

Finally, the subject invention provides a pair of reverse transcriptase polymerase chain reaction oligonucleotide primers for detecting the expression of the prostate specific antigen, wherein one such primer is an oligonucleotide 12 to 30 nucleotides in length and having the sequence 5'-X-CACCCCATCCTA-Y-3' and the second such primer is an oligonucleotide 12 to 30 nucleotides in length and having the nucleotide sequence 5'-X'-TCCAGCCACGAC-Y'-3' wherein each of X, X', Y, and Y' may be present or absent, but if present X is A, GA, AGA, CAGA, ACAGA, CACAGA, ACACAGA, AACACAGA, TAACACAGA, ATAACACAGA, AATAACACAGA, AAATAACACAGA, or CAAATAACACAGA; X' is C, AC, GAC, TGAC, ATGAC, GATGAC, TGATGAC, GTGATGAC, GGTGATGAC, AGGTGATGAC or CAGGTGATGAC; Y is T, TC, TCT, TCTG, TCTGT, or TCTGTG; and Y' is C, CT, CTC, CTCA, CTCAT, CTCATG, or CTCATGC.

BRIEF DESCRIPTION OF THE FIGURES

FIG. 4. Inability to detect PSA synthesizing cells in peripheral blood lymphocytes of females. Total RNA was extracted from the lymphocyte fraction of 6 females. These RNAs were assayed by RT-PCR using PSA primers. None of these specimens yielded a positive fragment by ethidium bromide visualization (top panel) or by the enhanced method (now shown). All specimens did yield an appropriate reaction product when G3PDH primers were utilized in the PCR reaction (bottom panel).

FIG. 5. Comparison of RT-PCR and enhanced RT-PCR for detection of PSA-synthesizing cells in the peripheral blood of 23 individual prostate cancer patients. Top panels; total RNA was extracted from peripheral blood lymphocytes of patients with localized and metastatic prostate cancer. This RNA was assayed by RT-PCR for PSA. Three specimens, as well as the LNCaP and prostate tumor control RNA demonstrate the presence of this fragment following ethidium bromide staining of the agarose gel. Bottom panels; demonstrate enhanced detection of the 710 bp PSA fragment. Luminescent substrate and autoradiography allowed the detection of 7 additional positive specimens in this group of patients.

FIG. 6. Nucleic acid sequence of the cDNA encoding the PSA protein. Sequence ID No. 1 (see Sequence ID No. 2 for the corresponding amino acid sequence).

DETAILED DESCRIPTION OF THE INVENTION

Figure 1:
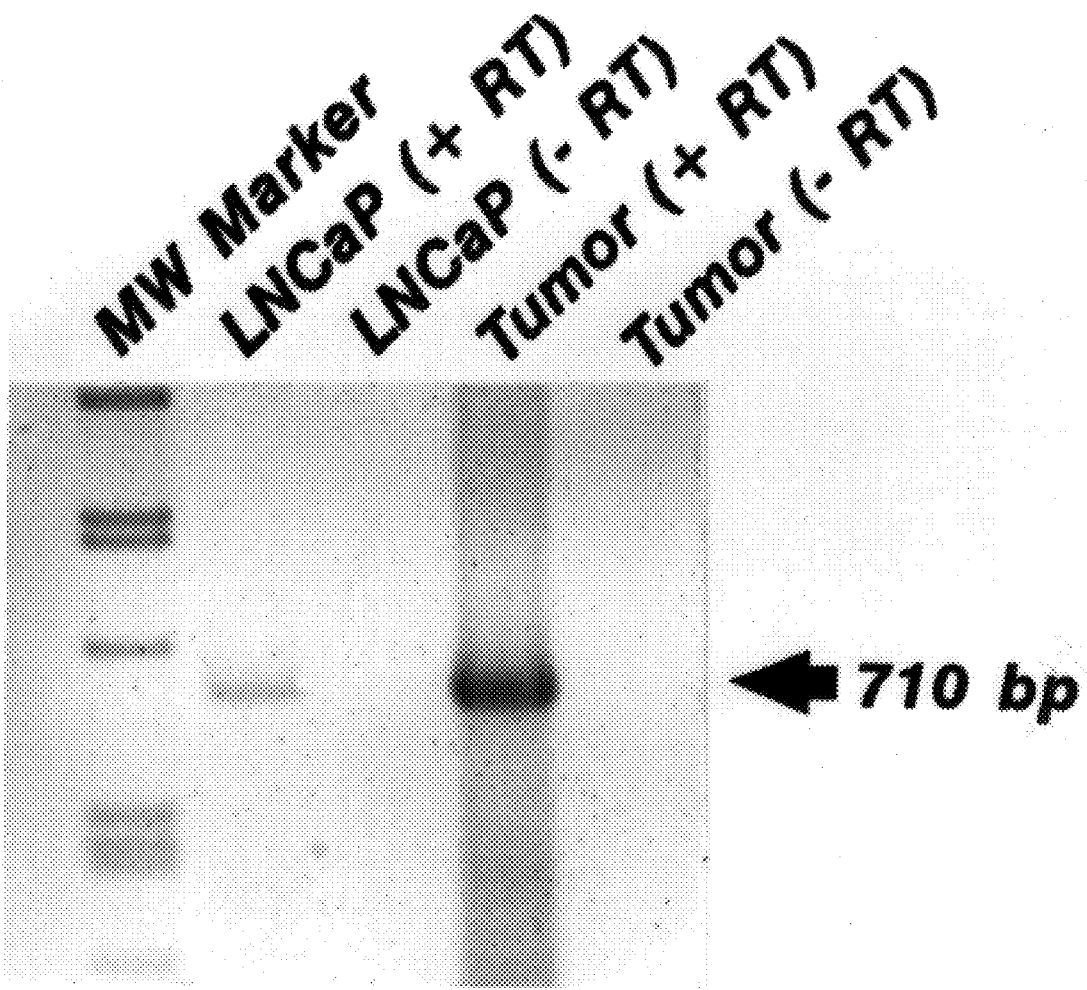
FIG. 1. RT-PCR assay identifies expression of PSA in the LNCaP cell line in a specimen of human prostate cancer. Total RNA was extracted from LNCaP cells and from a human prostate tumor. Aliquots were assayed for the presence of the diagnostic 710 bp PSA-specific PCR DNA fragment following treatment with oligo-dT with (+RT) or without (−RT) reverse transcriptase. The 710 bp PSA fragment was detected by UV transillumination of the ethidium bromide stained agarose gel following electrophoresis.

This invention provides a method of determining the stage of prostate cancer in a human subject which comprises: collecting a sample of peripheral blood from a human subject; extracting mRNA molecules from the peripheral blood; amplifying a cDNA molecule encoding the PSA protein which comprises: (i) contacting the mRNA molecule extract with a nucleic acid molecule primer capable of specifically hybridizing to a nucleic acid sequence site included within the mRNA encoding the PSA protein under conditions allowing the primer to specifically hybridize to the mRNA encoding the PSA protein; (ii) contacting the composition of (i) with reverse transcriptase under conditions allowing the reverse transcriptase to transcribe a single stranded cDNA molecule copy of the mRNA molecule encoding the PSA protein; (iii) heat denaturing the cDNA and mRNA molecule of composition (ii); (iv) contacting the composition of (iii) with a first primer capable of specifically hybridizing to a first unique nucleic acid molecule sequence site located on the cDNA molecule complementary to the mRNA encoding the PSA protein under conditions allowing the first primer to specifically hybridize with the first unique nucleic acid molecule sequence site; (v) contacting the composition of (iv) with DNA polymerase under conditions allowing the DNA polymerase to synthesize a double stranded cDNA molecule encoding the PSA protein using the first primer to initiate synthesis and the single-stranded cDNA molecule as a template; (vi) heat denaturing the double-stranded cDNA molecule of composition (v); (vii) contacting the composition of (vi) with the first primer and a second nucleic acid molecule primer capable of specifically hybridizing with a second unique nucleic acid molecule sequence site wherein the second unique nucleic acid sequence site is located on the other cDNA strand 3' of the first unique site under conditions allowing the first and second primers to specifically hybridize with the first and second unique sequences, respectively, of the cDNA molecule encoding the PSA protein; (viii) contacting the composition of (vii) with DNA polymerase under conditions allowing the DNA polymerase to synthesis cDNA molecules encoding the PSA protein using the first or second primers to initiate synthesis and the heat denatured cDNA molecule encoding the PSA protein as a template; and (ix) repeating steps (vi) through (viii) for at least twenty five times; and detecting the presence of the cDNA molecule encoding the PSA protein and thereby determining the stage of prostate cancer.

As used herein, the phrase "specifically hybridizing" means the ability of a nucleic acid molecule to recognize a nucleic acid sequence sufficiently similar to its own so as to form double-helical segments through hydrogen bonding between complementary base pairs. As used herein, a "unique sequence" is a sequence specific to only the nucleic acid molecules encoding the PSA protein.

The collection of blood from a patient is described in the Experimental Details. An adequate blood sample is 5–8 cc of peripheral blood. Although venous collection is discussed, peripheral blood can be drawn from arteries using methods known to one of skill in the art.

An example of one mRNA extraction procedure is provided in the Experimental Details, but the extraction of mRNA from a blood sample is well known to one of skill in the art and other methods can be used.

The preferred DNA polymerase is Taq Polymerase which is commercially available and has the additional benefit of retaining activity after exposure to DNA denaturing temperatures.

The determination that a human subject has PSA expressing cells circulating in the subjects peripheral blood can be made by detecting a cDNA product using the Method described hereinabove that consists of a base pair size predicted by the primers used and the known sequence of cDNA encoding the PSA protein. If primers other than those described in the Experimental Details are used, verification of the cDNA product produced should be done by sequencing the cDNA product.

This invention provides a method of determining the stage of prostate cancer in a human subject which comprises: collecting a sample of peripheral blood from a human subject; extracting mRNA molecules from the peripheral blood; amplifying a cDNA molecule encoding the PSA protein which comprises: (i) contacting the mRNA molecule extract with a nucleic acid molecule primer capable of specifically hybridizing to a nucleic acid sequence site included within the mRNA encoding the PSA protein under conditions allowing the primer to specifically hybridize to the mRNA encoding the PSA protein; (ii) contacting the composition of (i) with reverse transcriptase under conditions allowing the reverse transcriptase to transcribe a single stranded cDNA molecule copy of the mRNA molecule encoding the PSA protein; (iii) heat denaturing the cDNA and mRNA molecule of composition (ii); (iv) contacting the composition of (iii) with a first primer capable of specifically hybridizing to a first unique nucleic acid molecule sequence site located on the cDNA molecule complementary to the mRNA encoding the PSA protein under conditions allowing the first primer to specifically hybridize with the first unique nucleic acid molecule sequence site; (v) contacting the composition of (iv) with DNA polymerase under conditions allowing the DNA polymerase to synthesize a double stranded cDNA molecule encoding the PSA protein using the first primer to initiate synthesis and the single-stranded cDNA molecule as a template; (vi) heat denaturing the double-stranded cDNA molecule of composition (v); (vii) contacting the composition of (vi) with the first primer and a second nucleic acid molecule primer capable of specifically hybridizing with a second unique nucleic acid molecule sequence site wherein the second unique nucleic acid sequence site is located on the other cDNA strand 3' of the first unique site under conditions allowing the first and second primers to specifically hybridize with the first and second unique sequences, respectively, of the cDNA molecule encoding the PSA protein; (viii) contacting the composition of (vii) with DNA polymerase under conditions allowing the DNA polymerase to synthesis cDNA molecules encoding the PSA protein using the first or second primers to initiate synthesis and the heat denatured cDNA molecule encoding the PSA protein as a template; and (ix) repeating steps (vi) through (viii) for at least twenty five times; and detecting the presence of the cDNA molecule encoding the PSA protein which further comprises: loading the composition of step (ix) onto a gel; electrophoresing the cDNA into the gel with a DNA ladder; ethidium bromide staining the DNA inside the gel; visualizing the ethidium bromide stained DNA under ultraviolet light; and detecting the presence of the cDNA molecule encoding the PSA protein and thereby determining the stage of prostate cancer.

This invention provides a method of determining the stage of prostate cancer in a human subject which comprises: collecting a sample of peripheral blood from a human subject; extracting mRNA molecules from the peripheral blood; amplifying a cDNA molecule encoding the PSA protein which comprises: (i) contacting the mRNA molecule extract with a nucleic acid molecule primer capable of specifically hybridizing to a nucleic acid sequence site included within the mRNA encoding the PSA protein under conditions allowing the primer to specifically hybridize to the mRNA encoding the PSA protein; (ii) contacting the composition of (i) with reverse transcriptase under conditions allowing the reverse transcriptase to transcribe a single stranded cDNA molecule copy of the mRNA molecule encoding the PSA protein; (iii) heat denaturing the cDNA and mRNA molecule of composition (ii); (iv) contacting the composition of (iii) with a first primer capable of specifically hybridizing to a first unique nucleic acid molecule sequence site located on the cDNA molecule complementary to the mRNA encoding the PSA protein under conditions allowing the first primer to specifically hybridize with the first unique nucleic acid molecule sequence site; (v) contacting the composition of (iv) with DNA polymerase under conditions allowing the DNA polymerase to synthesize a double stranded cDNA molecule encoding the PSA protein using the first primer to initiate synthesis and the single-stranded cDNA molecule as a template; (vi) heat denaturing the double-stranded cDNA molecule of composition (v); (vii) contacting the composition of (vi) with the first primer and a second nucleic acid molecule primer capable of specifically hybridizing with a second unique nucleic acid molecule sequence site wherein the second unique nucleic acid sequence site is located on the other cDNA strand 3' of the first unique site under conditions allowing the first and second primers to specifically hybridize with the first and second unique sequences, respectively, of the cDNA molecule encoding the PSA protein; (viii) contacting the composition of (vii) with DNA polymerase under conditions allowing the DNA polymerase to synthesis cDNA molecules encoding the PSA protein using the first or second primers to initiate synthesis and the heat denatured cDNA molecule encoding the PSA protein as a template; and (ix) repeating steps (vi) through (viii) for at least twenty five times; and detecting the presence of the cDNA molecule encoding the PSA protein which comprises: adding digoxigenin-labeled nucleotides in step (iv); loading the composition of step (ix) which contains digoxigenin-labeled nucleotides onto a gel; electrophoresing the cDNA into the gel with a digoxigenin-labeled DNA ladder; transferring and fixing the DNA in the gel onto a membrane; contacting the DNA on the gel with an antibody which specifically binds digoxigenin, wherein the antibody is linked to an enzyme capable of directly or indirectly activating a chemiluminescent substrate; contacting the antibody bound DNA with the activatable chemiluminescent substrate; visualizing the presence of labeled DNA by exposing the membrane to a light sensitive device; and detecting the presence of the cDNA molecule encoding the PSA protein and thereby determining the stage of prostate cancer.

A preferred embodiment of the method to determining the stage of prostate cancer in a human subject comprises an enzyme capable of activating a chemiluminescent substrate which may be alkaline phosphatase, a the chemiluminescent substrate which may be 4-methoxy-4-(3-phosphate-phenyl)-spiro(1,2-dioxetane-3,2-adamantane) disodium salt, and a light sensitive device which may be X-ray film. Other light sensitive devices are known to those of skill in the art for recording labeled nucleotides, whether they be digoxigenin or radioactively labeled.

This invention provides a method of determining the stage of prostate cancer in a human subject which comprises: collecting a sample of peripheral blood from a human subject; extracting mRNA molecules from the peripheral blood; amplifying a cDNA molecule encoding the PSA protein which comprises: (i) contacting the mRNA molecule extract with a nucleic acid molecule primer capable of specifically hybridizing to a nucleic acid sequence site included within the mRNA encoding the PSA protein under conditions allowing the primer to specifically hybridize to the mRNA encoding the PSA protein; (ii) contacting the composition of (i) with reverse transcriptase under conditions allowing the reverse transcriptase to transcribe a single stranded cDNA molecule copy of the mRNA molecule encoding the PSA protein; (iii) heat denaturing the cDNA and mRNA molecule of composition (ii); (iv) contacting the composition of (iii) with a first primer capable of specifically hybridizing to a first unique nucleic acid molecule sequence site located on the cDNA molecule complementary to the mRNA encoding the PSA protein under conditions allowing the first primer to specifically hybridize with the first unique nucleic acid molecule sequence site, wherein the first primer comprises a nucleic acid molecule sequence of at least 15 nucleic acids that is the same or substantially the same as the nucleic acid sequence shown in FIG. 6; (v) contacting the composition of (iv) with DNA polymerase under conditions allowing the DNA polymerase to synthesize a double stranded cDNA molecule encoding the PSA protein using the first primer to initiate synthesis and the single-stranded cDNA molecule as a template; (vi) heat denaturing the double-stranded cDNA molecule of composition (v); (vii) contacting the composition of (vi) with the first primer and a second nucleic acid molecule primer capable of specifically hybridizing with a second unique nucleic acid molecule sequence site wherein the second unique nucleic acid sequence site is located on the other cDNA strand 3' of the first unique site under conditions allowing the first and second primers to specifically hybridize with the first and second unique sequences, respectively, of the cDNA molecule encoding the PSA protein; (viii) contacting the composition of (vii) with DNA polymerase under conditions allowing the DNA polymerase to synthesis cDNA molecules encoding the PSA protein using the first or second primers to initiate synthesis and the heat denatured cDNA molecule encoding the PSA protein as a template; and (ix) repeating steps (vi) through (viii) for at least twenty five times; and detecting the presence of the cDNA molecule encoding the PSA protein and thereby determining the stage of prostate cancer.

This invention provides a method of determining the stage of prostate cancer in a human subject which comprises: collecting a sample of peripheral blood from a human subject; extracting mRNA molecules from the peripheral blood; amplifying a cDNA molecule encoding the PSA protein which comprises: (i) contacting the mRNA molecule extract with a nucleic acid molecule primer capable of specifically hybridizing to a nucleic acid sequence site included within the mRNA encoding the PSA protein under conditions allowing the primer to specifically hybridize to the mRNA encoding the PSA protein; (ii) contacting the composition of (i) with reverse transcriptase under conditions allowing the reverse transcriptase to transcribe a single stranded cDNA molecule copy of the mRNA molecule encoding the PSA protein; (iii) heat denaturing the cDNA and mRNA molecule of composition (ii); (iv) contacting the composition of (iii) with a first primer capable of specifically hybridizing to a first unique nucleic acid molecule sequence site located on the cDNA molecule complementary to the mRNA encoding the PSA protein under conditions allowing the first primer to specifically hybridize with the first unique nucleic acid molecule sequence site; (v) contacting the composition of (iv) with DNA polymerase under conditions allowing the DNA polymerase to synthesize a double stranded cDNA molecule encoding the PSA protein using the first primer to initiate synthesis and the single-stranded cDNA molecule as a template; (vi) heat denaturing the double-stranded cDNA molecule of composition (v); (vii) contacting the composition of (vi) with the first primer and a second nucleic acid molecule primer capable of specifically hybridizing with a second unique nucleic acid molecule sequence site wherein the second unique nucleic acid sequence site is located on the other cDNA strand 3' of the first unique site under conditions allowing the first and second primers to specifically hybridize with the first and second unique sequences, respectively, of the cDNA molecule encoding the PSA protein, and wherein the second primer comprises a nucleic acid molecule sequence of at least 15 nucleic acids that is complementary to a nucleic acid molecule sequence that is the same or substantially the same as the nucleic acid sequence shown in FIG. 6; (viii) contacting the composition of (vii) with DNA polymerase under conditions allowing the DNA polymerase to synthesis cDNA molecules encoding the PSA protein using the first or second primers to initiate synthesis and the heat denatured cDNA molecule encoding the PSA protein as a template; and (ix) repeating steps (vi) through (viii) for at least twenty five times; and detecting the presence of the cDNA molecule encoding the PSA protein and thereby determining the stage of prostate cancer.

This invention provides a method of determining the stage of prostate cancer in a human subject which comprises: collecting a sample of peripheral blood from a human subject; extracting mRNA molecules from the peripheral blood; amplifying a cDNA molecule encoding the PSA protein which comprises: (i) contacting the mRNA molecule extract with a nucleic acid molecule primer capable of specifically hybridizing to a nucleic acid sequence site included within the mRNA encoding the PSA protein under conditions allowing the primer to specifically hybridize to the mRNA encoding the PSA protein; (ii) contacting the composition of (i) with reverse transcriptase under conditions allowing the reverse transcriptase to transcribe a single stranded cDNA molecule copy of the mRNA molecule encoding the PSA protein; (iii) heat denaturing the cDNA and mRNA molecule of composition (ii); (iv) contacting the composition of (iii) with a first synthesized oligonucleotide primer capable of specifically hybridizing to a first unique nucleic acid molecule sequence site located on the cDNA molecule complementary to the mRNA encoding the PSA protein under conditions allowing the first primer to specifically hybridize with the first unique nucleic acid molecule sequence site; (v) contacting the composition of (iv) with DNA polymerase under conditions allowing the DNA polymerase to synthesize a double stranded cDNA molecule encoding the PSA protein using the first primer to initiate synthesis and the single-stranded cDNA molecule as a template; (vi) heat denaturing the double-stranded cDNA molecule of composition (v); (vii) contacting the composition of (vi) with the first primer and a second synthesized oligonucleotide primer capable of specifically hybridizing with a second unique nucleic acid molecule sequence site wherein the second unique nucleic acid sequence site is located on the other cDNA strand 3' of the first unique site under conditions allowing the first and second primers to specifically hybridize with the first and second unique sequences, respectively, of the cDNA molecule encoding the PSA protein; (viii) contacting the composition of (vii) with DNA polymerase under conditions allowing the DNA polymerase to synthesis cDNA molecules encoding the PSA protein using the first or second primers to initiate synthesis and the heat denatured cDNA molecule encoding the PSA protein as a template; and (ix) repeating steps (vi) through (viii) for at least twenty five times; and detecting the presence of the cDNA molecule encoding the PSA protein and thereby determining the stage of prostate cancer.

The preferred embodiment of the first synthesized oligonucleotide primer is a synthesized oligonucleotide primer comprising a nucleic acid molecule with a nucleotide sequence of 5'-GATGACTCCAGCCACGACCT-3' Sequence ID No. 4.

The preferred embodiment of the second synthesized oligonucleotide primer is a synthesized oligonucleotide primer comprising a nucleic acid molecule with a nucleotide sequence of 5'-CACAGACACCCCATCCTATC-3' Sequence ID No. 3.

The most preferred embodiment of first and second nucleic acid molecule primers is a first primer with a nucleotide sequence of 5'-GATGACTCCAGCCACGACCT-3', and a second nucleic acid molecule primer with a nucleotide sequence of 5'-CACAGACACCCCATCCTATC-3', wherein the use of these two primers in the hereinabove disclosed methods for determining the stage of prostate cancer in a human subject produces an amplified cDNA which is 710 base pairs long.

This invention provides a method of determining the stage of prostate cancer in a human subject which comprises: collecting a sample of peripheral blood from a human subject; extracting mRNA molecules from the peripheral blood; amplifying a cDNA molecule encoding the PSA protein which comprises: (i) contacting the mRNA molecule extract with a nucleic acid molecule primer capable of specifically hybridizing to a nucleic acid sequence site included within the mRNA encoding the PSA protein under conditions allowing the primer to specifically hybridize to the mRNA encoding the PSA protein, wherein the primer capable of specifically hybridizing the mRNA encoding the PSA protein is an oligo(dT)$_N$, primer; (ii) contacting the composition of (i) with reverse transcriptase under conditions allowing the reverse transcriptase to transcribe a single stranded cDNA molecule copy of the mRNA molecule encoding the PSA protein; (iii) heat denaturing the cDNA and mRNA molecule of composition (ii); (iv) contacting the composition of (iii) with a first primer capable of specifically hybridizing to a first unique nucleic acid molecule sequence site located on the cDNA molecule complementary to the mRNA encoding the PSA protein under conditions allowing the first primer to specifically hybridize with the first unique nucleic acid molecule sequence site; (v) contacting the composition of (iv) with DNA polymerase under conditions allowing the DNA polymerase to synthesize a double stranded cDNA molecule encoding the PSA protein using the first primer to initiate synthesis and the single-stranded cDNA molecule as a template; (vi) heat denaturing the double-stranded cDNA molecule of composition (v); (vii) contacting the composition of (vi) with the first primer and a second nucleic acid molecule primer capable of specifically hybridizing with a second unique nucleic acid molecule sequence site wherein the second unique nucleic acid sequence site is located on the other cDNA strand 3' of the first unique site under conditions allowing the first and second primers to specifically hybridize with the first and second unique sequences, respectively, of the cDNA molecule encoding the PSA protein; (viii) contacting the composition of (vii) with DNA polymerase under conditions allowing the DNA polymerase to synthesis cDNA molecules encoding the PSA protein using the first or second primers to initiate synthesis and the heat denatured cDNA molecule encoding the PSA protein as a template; and (ix) repeating steps (vi) through (viii) for at least twenty five times; and detecting the presence of the cDNA molecule encoding the PSA protein and thereby determining the stage of prostate cancer.

As used herein a oligo(dT)$_N$ primer is an oligonucleotide primer consisting of sequence of thymidine base pairs where N equals 12–18.

This invention provides a method of determining the stage of prostate cancer in a human subject which comprises: collecting a sample of peripheral blood from a human subject, wherein the peripheral blood contains PSA expressing cells at a concentration equal to or greater than one PSA expressing cell per 100,000 blood cells; extracting mRNA molecules from the peripheral blood; amplifying a cDNA molecule encoding the PSA protein which comprises: (i) contacting the mRNA molecule extract with a nucleic acid molecule primer capable of specifically hybridizing to a nucleic acid sequence site included within the mRNA encoding the PSA protein under conditions allowing the primer to specifically hybridize to the mRNA encoding the PSA protein; (ii) contacting the composition of (i) with reverse transcriptase under conditions allowing the reverse transcriptase to transcribe a single stranded cDNA molecule copy of the mRNA molecule encoding the PSA protein; (iii) heat denaturing the cDNA and mRNA molecule of composition (ii); (iv) contacting the composition of (iii) with a first primer capable of specifically hybridizing to a first unique nucleic acid molecule sequence site located on the cDNA molecule complementary to the mRNA encoding the PSA protein under conditions allowing the first primer to specifically hybridize with the first unique nucleic acid molecule sequence site; (v) contacting the composition of (iv) with DNA polymerase under conditions allowing the DNA polymerase to synthesize a double stranded cDNA molecule encoding the PSA protein using the first primer to initiate synthesis and the single-stranded cDNA molecule as a template; (vi) heat denaturing the double-stranded cDNA molecule of composition (v); (vii) contacting the composition of (vi) with the first primer and a second nucleic acid molecule primer capable of specifically hybridizing with a second unique nucleic acid molecule sequence site wherein the second unique nucleic acid sequence site is located on the other cDNA strand 3' of the first unique site under conditions allowing the first and second primers to specifically hybridize with the first and second unique sequences, respectively, of the cDNA molecule encoding the PSA protein; (viii) contacting the composition of (vii) with DNA polymerase under conditions allowing the DNA polymerase to synthesis cDNA molecules encoding the PSA protein using the first or second primers to initiate synthesis and the heat denatured cDNA molecule encoding the PSA protein as a template; and (ix) repeating steps (vi) through (viii) for at least twenty five times; and detecting the presence of the cDNA molecule encoding the PSA protein and thereby determining the stage of prostate cancer.

The subject invention also provides a method for enhancing the detection of prostate specific antigen in a biological sample suspected of containing prostate specific antigen which comprises:

(a) extracting mRNA from the sample;

(b) contacting the mRNA from step (a) with reverse transcriptase under conditions allowing for the production of cDNA;

(c) contacting the cDNA from step (b) with a pair of reverse transcriptase polymerase chain reaction oligonucleotide primers capable of specifically hybridizing with DNA encoding prostate specific antigen, wherein one such primer is an oligonucleotide 12 to 30 nucleotides in length and having the sequence 5'-X-CACCCCATCCTA-Y-3' and the second such primer is an oligonucleotide 12 to 30 nucleotides in length and having the nucleotide sequence 5'-X'-TCCAGCCACGAC-Y'-3' wherein each of X, X', Y, and Y' may be present or absent, but if present X is A, GA, AGA, CAGA, ACAGA, CACAGA, ACACAGA, AACACAGA, TAACACAGA, ATAACACAGA, AATAACACAGA, AAATAACACAGA, or CAAATAACACAGA; X' is C, AC, GAC, TGAC, ATGAC, GATGAC, TGATGAC, GTGATGAC, GGTGATGAC, AGGTGATGAC or CAGGTGATGAC; Y is T, TC, TCT, TCTG, TCTGT, or TCTGTG; and Y' is C, CT, CTC, CTCA, CTCAT, CTCATG, or CTCATGC; and wherein at least one of the primers is covalently linked to a suitably modified digoxigenin molecule, under conditions allowing for hybridization of both primers to any cDNA encoding prostate specific antigen so as to obtain a double stranded duplex comprising the cDNA hybridized to the primers;

(d) contacting the double stranded duplex from step (c) with DNA polymerase under conditions allowing for the extension of the primers to produce cDNA encoding prostate specific antigen and comprising a suitably modified digoxigenin molecule; and (e) detecting the suitably modified digoxigenin molecule from the cDNA from step (d) thereby detecting prostate specific antigen.

In a preferred embodiment of the above described method the first primer is 5'-CACAGACACCCCATCCTATC-3' and the second primer is 5'-GATGACTCCAGCCACGACCT-3'.

Those skilled in the art will recognize that steps (a) and (b), extracting mRNA from a biological and production of complementary DNA (cDNA) from the extracted mRNA, respectively, as recited in the above described method and the methods described hereinbelow, are well known to those of ordinary skill in the art. For an example of such methods and the suitable conditions for carrying them out, see J. Sambrook, E. F. Fritsch, and T. Maniatis, Molecular Cloning, A Laboratory Manual 2 ed. (Cold Spring Harbor Laboratory Press, Cold Spring Harbor, N.Y.: 1989).

Those skilled in the art will recognize that the methods of "contacting" recited in steps (c) and (d) as well as the suitable "conditions" for carrying out the steps of the above described method and the methods described hereinbelow are readily determinable by those of ordinary skill in the art. Examples of these methods and suitable conditions can be found in PCR Protocols, A Guide to Methods and Applications, Innis, M., Gelfand, D., Sninsky, J, and White, T., eds. (Academic Press, San Diego, Calif.: 1990). The term "double stranded duplex" as used herein refers to the composition of matter obtained when the primers have specifically hybridized to the cDNA encoding prostate specific antigen prior to the extension of the primers.

In a preferred embodiment of the above described method the detection in step (e) is accomplished using a detectably labeled antibody which specifically binds to the suitably modified digoxigenin molecule. As used herein a "suitably modified digoxigenin molecule" refers to the resulting chemical moiety which is covalently attached to a molecule of interest when labeling the molecule of interest with a digoxigenin label. The digoxigenin label is thereafter used as a means of detecting the molecule of interest by methods of detecting the suitably modified digoxigenin molecule. Such methods include, but are not limited to use of antibodies which specifically bind to the suitably modified digoxigenin molecule. Methods of attaching a digoxigenin label, and, therefore, covalently linking a suitably modified digoxigenin molecule to a molecule of interest, are well known to those of ordinary skill in the art. An example of the use of digoxigenin labels is included in the Experimental Details below.

Suitable labels for antibodies to allow for their detection in assays of this type are known to those of skill in the art and include, but are not limited to, enzymes, dyes, fluorescent markers such as fluorophores and chromaphores, colored bead, radioactive isotope or biotin.

In a preferred embodiment the above described method the detectably labeled antibody is labeled with an enzyme. Examples of enzymes useful as labels for detectably labeling antibodies include, but are not limited to, peroxidase, such as horseradish peroxidase, or other enzymes such as alkaline phosphatase and B-galactosidase. In a particularly preferred embodiment of the subject invention the enzyme is alkaline phosphatase.

In the practice of the above described method the biological sample can be taken from the peripheral blood or lymph nodes of a subject. Use of either type of samples represents independently preferred embodiments of the subject invention.

The subject invention also provides a method for detecting prostate specific antigen in a biological sample suspected of containing prostate specific antigen which comprises:

(a) extracting mRNA from the sample;

(b) contacting the mRNA from step (a) with reverse transcriptase under conditions allowing for the production of cDNA;

(c) contacting the cDNA from step (b) with a pair of reverse transcriptase polymerase chain reaction oligonucleotide primers capable of specifically hybridizing with DNA encoding prostate specific antigen, wherein one such primer is an oligonucleotide 12 to 30 nucleotides in length and having the sequence 5'-X-CACCCCATCCTA-Y-3' and the second such primer is an oligonucleotide 12 to 30 nucleotides in length and having the nucleotide sequence5'-X'-TCCAGCCACGAC-Y'-3' wherein each of X, X', Y, and Y' may be present or absent, but if present X is A, GA, AGA, CAGA, ACAGA, CACAGA, ACACAGA, AACACAGA, TAACACAGA, ATAACACAGA, AATAACACAGA, AAATAACACAGA, or CAAATAACACAGA; X' is C, AC, GAC, TGAC, ATGAC, GATGAC, TGATGAC, GTGATGAC, GGTGATGAC, AGGTGATGAC or CAGGTGATGAC; Y is T, TC, TCT, TCTG, TCTGT, or TCTGTG; and Y' is C, CT, CTC, CTCA, CTCAT, CTCATG, or CTCATGC; under conditions allowing for hybridization of both primers to any cDNA encoding prostate specific antigen so as to obtain a double stranded duplex comprising the cDNA hybridized to the primers;

(d) contacting the double stranded duplex from step (c) with DNA polymerase under conditions allowing for the extension of the primers to produce cDNA encoding prostate specific antigen; and (e) detecting the cDNA from step (d) thereby detecting prostate specific antigen.

In a preferred embodiment of the above described method the first primer is 5'-CACAGACACCCCATCCTATC-3' and the second primer is 5'-GATGACTCCAGCCACGACCT-3'.

In one preferred embodiment the biological sample is a sample taken from the peripheral blood of a subject. In a second preferred embodiment the biological sample is a sample from the lymph nodes of a subject.

The subject invention further provides a method of diagnosing prostate cancer in a subject which comprises:

(a) obtaining a biological sample from the subject;

(b) extracting mRNA from the sample;

(c) contacting the mRNA from (b) with reverse transcriptase under conditions allowing for the production of cDNA;

(d) contacting the cDNA from step (c) with a pair of reverse transcriptase polymerase chain reaction oligonucleotide primers capable of specifically hybridizing with DNA encoding prostate specific antigen, wherein one such primer is an oligonucleotide 12 to 30 nucleotides in length and having the sequence 5'-X-CACCCCATCCTA-Y-3' and the second such primer is an oligonucleotide 12 to 30 nucleotides in length and having the nucleotide sequence 5'-X'-

TCCAGCCACGAC-Y'-3' wherein each of X, X', Y, and Y' may be present or absent, but if present X is A, GA, AGA, CAGA, ACAGA, CACAGA, ACACAGA, AACACAGA, TAACACAGA, ATAACACAGA, AATAACACAGA, AAATAACACAGA, or CAAATAACACAGA; X' is C, AC, GAC, TGAC, ATGAC, GATGAC, TGATGAC, GTGATGAC, GGTGATGAC, AGGTGATGAC or CAG-GTGATGAC; Y is T, TC, TCT, TCTG, TCTGT, or TCT-GTG; and Y' is C, CT, CTC, CTCA, CTCAT, CTCATG, or CTCATGC; under conditions allowing for hybridization of both primers to any cDNA encoding prostate specific antigen so as to obtain a double stranded duplex comprising the cDNA hybridized to the primers;

(e) contacting the double stranded duplex from step (d) with DNA polymerase under conditions allowing for the extension of the primers to produce cDNA encoding prostate specific antigen; and (f) detecting the cDNA from step (e) thereby diagnosing prostate cancer in the subject.

In a preferred embodiment of the above described method the first primer is 5'-CACAGACACCCCATCCTATC-3' and the second primer is 5'-GATGACTCCAGCCACGACCT-3'.

In a preferred embodiment of the above described method at least one of the primers in the set of reverse transcriptase polymerase chain reaction primers is covalently linked to a suitably modified digoxigenin molecule.

In another preferred embodiment, the detection of cDNA in step (f) in the above described method comprises detection of the suitably modified digoxigenin molecule with a detectably labeled antibody which specifically binds to the suitably modified digoxigenin molecule.

Suitable labels for antibodies to allow for their detection in assays of this type are known to those of skill in the art and include, but are not limited to, enzymes, dyes, fluorescent markers such as fluorophores and chromaphores, colored bead, radioactive isotope or biotin.

In a preferred embodiment the above described method the detectably labeled antibody is labeled with an enzyme. Examples of enzymes useful as labels for detectably labeling antibodies include, but are not limited to, peroxidase, such as horseradish peroxidase, or other enzymes such as alkaline phosphatase and β-galactosidase. In a particularly preferred embodiment of the subject invention the enzyme is alkaline phosphatase.

In one preferred embodiment of the above described method the biological sample is a sample taken from the peripheral blood of a subject. In a second preferred embodiment the biological sample is a sample from the lymph nodes of a subject.

The subject invention further provides a method of determining the stage of prostate cancer in a subject which comprises:

(a) obtaining a biological sample from the subject;

(b) extracting mRNA from the sample;

(c) contacting the mRNA from (b) with reverse transcriptase under conditions allowing for the production of cDNA;

(d) contacting the cDNA from step (c) with a pair of reverse transcriptase polymerase chain reaction oligonucleotide primers capable of specifically hybridizing with DNA encoding prostate specific antigen, wherein one such primer is an oligonucleotide 12 to 30 nucleotides in length and having the sequence 5'-X-CACCCCATCCTA-Y-3' and the second such primer is an oligonucleotide 12 to 30 nucleotides in length and having the nucleotide sequence 5'-X'-TCCAGCCACGAC-Y'-3' wherein each of X, X', Y, and Y' may be present or absent, but if present X is A, GA, AGA, CAGA, ACAGA, CACAGA, ACACAGA, AACACAGA, TAACACAGA, ATAACACAGA, AATAACACAGA, AAATAACACAGA, or CAAATAACACAGA; X' is C, AC, GAC, TGAC, ATGAC, GATGAC, TGATGAC, GTGATGAC, GGTGATGAC, AGGTGATGAC or CAG-GTGATGAC; Y is T, TC, TCT, TCTG, TCTGT, or TCT-GTG; and Y' is C, CT, CTC, CTCA, CTCAT, CTCATG, or CTCATGC; under conditions allowing for hybridization of both primers to any cDNA encoding prostate specific antigen so as to obtain a double stranded duplex comprising the cDNA hybridized to the primers;

(e) contacting the double stranded duplex from step (d) with DNA polymerase under conditions allowing for the extension of the primers to produce cDNA encoding prostate specific antigen; and (f) detecting the cDNA from step (e) thereby determining the stage of prostate cancer in the subject.

In a preferred embodiment of the above described method the first primer is 5'-CACAGACACCCCATCCTATC-3' and the second primer is 5'-GATGACTCCAGCCACGACCT-3'.

In another preferred embodiment at least one of the primers in the pair of reverse transcriptase polymerase chain reaction oligonucleotide primers is covalently linked to a suitably modified digoxigenin molecule.

In a preferred embodiment of the above described method the detection of cDNA in step (f) comprises detection of the suitably modified digoxigenin molecule with a detectably labeled antibody which specifically binds to the suitably modified digoxigenin molecule.

Suitable labels for antibodies to allow for their detection in assays of this type are known to those of skill in the art and include, but are not limited to, enzymes, dyes, fluorescent markers such as fluorophores and chromaphores, colored bead, radioactive isotope or biotin.

In a preferred embodiment the above described method the detectably labeled antibody is labeled with an enzyme. Examples of enzymes useful as labels for detectably labeling antibodies include, but are not limited to, peroxidase, such as horseradish peroxidase, or other enzymes such as alkaline phosphatase and β-galactosidase. In a particularly preferred embodiment of the subject invention the enzyme is alkaline phosphatase.

In one preferred embodiment of the above described method the biological sample is a sample taken from the peripheral blood of a subject. In a second preferred embodiment the biological sample is a sample from the lymph nodes of a subject.

The subject invention also provides an oligonucleotide 12 to 30 nucleotides in length and having the sequence 5'-X-CACCCCATCCTA-Y-3' wherein each of X and Y may be present or absent, but if present X is A, GA, AGA, CAGA, ACAGA, CACAGA, ACACAGA, AACACAGA, TAACACAGA, ATAACACAGA, AATAACACAGA, AAATAACACAGA, or CAAATAACACAGA; and Y is T, TC, TCT, TCTG, TCTGT, or TCTGTG.

In a preferred embodiment the oligonucleotide has the nucleotide sequence 5'-CACAGACACCCCATCCTATC-3'.

In a preferred embodiment the oligonucleotide described above is covalently linked to a suitably modified digoxigenin molecule.

The subject invention further provides an oligonucleotide 12 to 30 nucleotides in length and having the nucleotide sequence 5'-X'-TCCAGCCACGAC-Y'-3' wherein each of X' and Y' may be present or absent, but if present X' is C, AC, GAC, TGAC, ATGAC, GATGAC, TGATGAC, GTGATGAC, GGTGATGAC, AGGTGATGAC or CAG-GTGATGAC; and Y' is C, CT, CTC, CTCA, CTCAT, CTCATG, or CTCATGC.

In a preferred embodiment the oligonucleotide has the nucleotide sequence 5'-GATGACTCCAGCCACGACCT-3'.

In a preferred embodiment the oligonucleotide described above is covalently linked to a suitably modified digoxigenin molecule.

Finally, the subject invention provides a pair of reverse transcriptase polymerase chain reaction oligonucleotide primers for detecting the expression of the prostate specific antigen, wherein one such primer is an oligonucleotide 12 to 30 nucleotides in length and having the sequence 5'-X-CACCCCATCCTA-Y-3' and the second such primer is an oligonucleotide 12 to 30 nucleotides in length and having the nucleotide sequence 5'-X'-TCCAGCCACGAC-Y'-3' wherein each of X, X', Y, and Y' may be present or absent, but if present X is A, GA, AGA, CAGA, ACAGA, CACAGA, ACACAGA, AACACAGA, TAACACAGA, ATAACACAGA, AATAACACAGA, AAATAACACAGA, or CAAATAACACAGA; X' is C, AC, GAC, TGAC, ATGAC, GATGAC, TGATGAC, GTGATGAC, GGTGATGAC, AGGTGATGAC or CAGGTGATGAC; Y is T, TC, TCT, TCTG, TCTGT, or TCTGTG; and Y' is C, CT, CTC, CTCA, CTCAT, CTCATG, or CTCATGC.

In a preferred embodiment of the pair of reverse transcriptase polymerase chain reaction oligonucleotide primers described above the first such primer is 5'-CACAGACACCCCATCCTATC-3' and the second such primer is 5'-GATGACTCCAGCCACGACCT-3'.

In another preferred embodiment of the pair of reverse transcriptase polymerase chain reaction oligonucleotide primers described above at least one of the primers is covalently linked to a suitably modified digoxigenin molecule.

The reverse transcriptase polymerase chain reaction oligonucleotide primers described above can be used as the pair described immediately above or individually with other primers known or later discovered by one of ordinary skill in the art. Such uses can include use of the primers as primary sequences or as nested primers to enhance specific amplification. Such uses are contemplated to be within the scope of the claimed invention.

The following Experimental Details, and examples contained therein, are set forth in an effort to further explain the invention. The examples are not intended to, and should not be interpreted to, limit in any way the scope of the invention which is more fully defined in the claims which follow thereafter.

EXPERIMENTAIL DETAILS

EXAMPLE 1—Detection of Prostate Specific Antigen

I. Experimental Methods

A. Human Materials and Patient Selection

Two groups of prostate cancer patients were examined during our study; Group 1 comprised 10 patients with untreated metastatic prostate cancers (T4) confirmed by markedly elevated PSA values and the detection of metastatic lesions on a bone scan. Group 2 consisted of 48 patients with clinically localized prostate cancer (T1-T2c) who were scheduled for radical retropubic prostatectomy. All of these patients had received a digital rectal examination and a serum PSA determination (Hybritech Inc., San Diego, Calif.) as well as a bone scan prior to surgery. In each case a CT scan and/or endorectal coil MRI was used for local staging of the tumor. Nine of the patients from group 2 received preoperative treatment with flutamide (750 mg/day) as a means to reduce bulky tumor mass prior to surgery. All physical examinations and surgical procedures for the patients in group 2 were performed by a single surgeon (CAO).

In addition to the prostate cancer patients, three groups of non-prostate cancer controls were analyzed: Group 1 comprised 20 females hospitalized at our institution, Group 2 consisted of 20 young males (ages 19–49) with no prior urological disease history, and Group 3 consisted of 25 age-matched males (ages 45–77, mean 62) that were under outpatient treatment for BPH. The age-matched control male patients all had serum PSA values less than 4.0 and negative digital rectal examinations. All patients and controls were evaluated at our institution, and their participation in this study was approved by the Internal Review Board.

B. Patient Samples

Venous blood (5 cc) was collected from each individual in EDTA-treated collection tubes, placed immediately on ice, and processed within 3 hours of phlebotomy. For surgical candidates, the samples were obtained usually 1 week prior to surgery, at least two weeks from digital rectal examination and two weeks from prostate needle biopsy. Samples were diluted with an equal volume of phosphate-buffered saline (PBS) and carefully layered onto 8 cc of Ficoll-Pack (Pharmacia Inc., Piscataway, N.J.). The sample was centrifuged at 400×g for 20 min., and the buffy coat cells were recovered. The cells were washed in 50 cc PBS and were re-centrifuged at 1000×g for 30 min to produce a cell pellet.

A surgical specimen containing human prostate cancer was obtained from the human tumor bank operated by the Department of Pathology at this institution. This tissue was excised from a radical prostatectomy specimen and was frozen in liquid nitrogen and stored at −90° C.

C. Cell Culture

The human PSA-expression LnCaP cell line was originally established from a patient with metastatic prostate cancer to the pelvic lymph nodes (11). Monolayer propagation of these cells was in RPMI media supplemented with 5% Fetal Bovine Serum (FBS), 100 units/ml of penicillin and 0.1 mg/ml streptomycin. Every 2 days the cells received fresh medium and confluent cultures were dispersed with trypsin (0.05%):EDTA (0.02%) solution for subsequent passage. Serial dilutions of trypsinized cells were made in PBS to achieve cell densities as follows: 10,000 cells per ml, 1000 cells per ml, 100 cells per ml, and 100 cells per ml. These dilutions were added to $10^6$ cultured immortalized B-cells (gift of R. Dalla Favera, Columbia University), centrifuged at 1500 rpm for 5 min., and prepared for RNA extraction.

D. RNA Extraction

Total RNA was obtained from these cells by a modification of the Guanididium thiocyanate/phenol/chloroform extraction technique (12) utilizing the RNAzole B reagent of Tel-Test, Inc., (Friendswood, Tex.). The RNA pellet obtained after ethanol/sodium acetate precipitation was dried under vacuum and dissolved in 50 μl of RNase-free water. Quantification of RNA was done based on spectrophotometric measurements at 260 nm.

E. Reverse Transcription Reaction

An aliquot containing 1 μg of total RNA was added to 0.5 μg of oligo(dT)$_{12-18}$ primer (Gibco, BRL, Life Technologies, Inc.(, and brought to a final volume of 20 μl. The samples were placed at 65° C. for 5 min., then chilled on ice for 5 min. The primer annealed RNA was added to 30 μl master reaction mixture so that the final concentration of the following components were achieved: 1 mM of each dNTP, 50 mM Tris-HCl (ph8.3), 75 mM KCl, 3 mM MgCl$_2$, 10 mM DTT, 10 units per reaction of Placental RNase inhibitor, and 200 units per reaction of M-MuLV Reverse Transcriptase (Superscript II, Gibco BRL). The reaction was incubated at 42° C. for 15 min. and the enzyme was heat inactivated at 95° C. for 15 seconds.

F. Polymerase Chain Reaction (PCR)

Oligonucleotide primers, specific for the human PSA cDNA coding region, were designed with the aid of the primer analysis software, OLIGO (version 4.0, National Biosciences, Plymouth, Minn.) and were synthesized by national Biosciences. The 18-base pair primers were designed to span across three exons; from exon 3 and extending into exon 5 with the following sequences:

PSA3': 5'-CACAGACACCCCATCCTATC-3'
PSA5': 5'-GATGACTCCAGCCACGACCT-3'

Oligonucleotide primers for human glyceraldehyde 3-phosphate dehydrogenase (G3PDH) were obtained from Clontech laboratories (Palo Alto, Calif.) and PCR for this gene produce was performed in a separate reaction for each sample. The PCR reaction was done in a total volume of Al containing one fifth of the RT reaction with a final concentration of the following reagents: 20 mM Tris-HCl (ph 8.3 at 20° C.), 50 mM KCl, 1.5 mM MgCl$_2$, 0.2 mM of each dNTP, 2.5 units of Taq Polymerase and 10 pmoles of each primer. When enhanced sensitivity was desired, digoxigenin-11-deoxyurdine Triphosphate (Dig-dUTP) (Boehringer Mannheim Corp., Indianapolis, Ind.) was added to a final concentration of 0.55 $\mu$M. All reactions were prepared with sets of PCR-dedicated micropipettors using plugged tips to protect against cross contamination.

A total of 35 cycles were completed with the following specification: A) cycle 1, 95° C. (4 min); B) cycles 2–16, 95° C. (1 min), 60° C. (1 min), 72° C. (1 min); D) cycles 28-24, 95° C. 1 min, 60° C. 1 min., 72° C. 2 min, and the last cycle was at 72° C. for 15 min. With the addition of Dig-dUTP in the PCR reaction the number of cycles was decreased to 25 with the removal of cycle set C. The PCR products were stored at 4° C. until electrophoresis. Aliquots of the reaction were electrophoresed on 2.5% agarose gels in TEA buffer at 80 V. The gels were stained with ethidium bromide and were viewed under UV light.

G. Cloning of the PSA-PCR Product

The 710 base pair band representing the PCR produce derived from a human prostate tumor was excised and purified from a 2.0% agarose gel. This PCR product was ligated into the PCR cloning site of the pCR II vector (Invitrogen Corp.). The cloned insert was sequenced using SP6 and T7 primers by dideoxy-nucleotide sequence analysis (13). The sequence obtained for this DNA insert was compared with the Human PSA genomic sequence of Klobeck, et al. (14) obtained in the Genebank (Accession # X14810).

H. Enhanced PCR Detection

Digoxigenin-enhanced detection of the PSA PCR reaction product was accomplished with the use of Genius DNA labeling kit (Boehringer Mannhein) with modifications. Southern blotting of the gel fractionated PCR reaction onto positively charged nylon membranes (Boehringer Mannheim) was accomplished following standard techniques (15) and was fixed onto the membrane by UV exposure. Membrane washing and blocking was according the manufacture's specifications. Alkaline phosphatase-conjugated anti-digoxigenin antibody (Fab fragment) was used at a 1:50,000 dilution in Genius 2 buffer (2% blocking agent in 100 mM Tris-HCl (ph 7.5 at 20° C.), 150 mM NaCl prior to incubation with the membrane. The chemiluminescent substrate, Lumi-Phos 530 [0.33 mM Lumigen PPD [4-methoxy-4-(3-phosphate-phenyl)-sprio(1,2-dioxetane-3, 2-adamantane) disodium salt]; 0.88 mM MgCL$_2$; 1.13 mM cetyltrimethy-ammonium bromide; 0.035 mM fluorescein surfactant], was diluted 1:1 in 100 mMTris-HCL (pH 9.5 at 20° C.), 100 mM NaCl, 50 mM MgCL$_2$ and a small amount was carefully spread across the membrane. The wrapped membrane was exposed to X-ray film, typically, for only several minutes and the film was developed.

I. Statistical Methods

Logistic regression analysis was used to determine the statistical significance of each of the following preoperative factors: PSA, PSAD, imaging (CT-scan and/or endorectal MRI), and PCR. A Chi-square score was determined for each independent variable to evaluate the likelihood of predicting margin positive-disease. In addition, preoperative factors were examined with and without the PCR assay to determine if deletion or addition of assay results would add to the prediction of margin positive disease.

II. Results

A. Detection of PSA-Synthesizing Cells by PCR

RNA was extracted from the LNCaP cell line and from a surgically-removed specimen containing prostate cancer. This RNA was reverse transcribed to cDNA and then utilized in a PCR reaction with primers designed to amplify a 710 bp DNA fragment from human PSA RNA. Following electrophoresis of the PCR products, we were able to identify the appropriate DNA fragment corresponding to PSA only in reactions containing cDNA (FIG. 1). This 710 bp fragment was cloned into a plasmid vector and was sequenced. The sequence of the insert (not shown here) corresponded at every nucleotide to the sequence of human PSA appearing in the genebank.

B. PCR of LnCaP Dilution

Figures 2A, 2B:
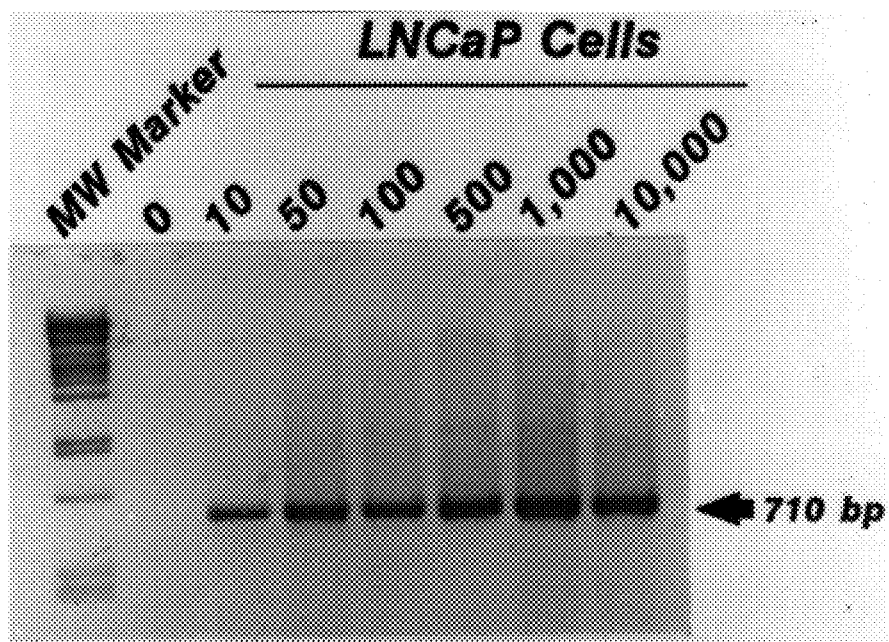
FIG. 2. Sensitivity of RT-PCR assay determined by analysis of diluted LNCaP cells. RNA was extracted from serial dilutions of LNCaP cells in $10^6$ cultured B lymphocytes and was assayed by RT-PCR for PSA. The 710 bp PSA-PCR fragment could be amplified only from specimens containing LNCaP cells (top panel). Human G3PDH primers were utilized in a parallel reaction and these primers amplified the appropriate 983 bp fragment from all specimens (lower panel).

By diluting known quantities of LnCaP cells into cultured B-lymphocytes, were able to evaluate the minimum number of PSA-synthesizing cells detectable by PCR> Serial dilutions of LNCaP cells were added to aliquots containing $10^6$ human B-lymphocytes. RNA was extracted from these diluted specimens and was assayed in individual reactions by RT-PCR. A portion of the reaction product was electrophoresed on an agarose gel and, as shown in FIG. 2, when the reaction included primers for human PSA, we could detect as few as 10 PSA-synthesizing cells (1 in 100,000). Duplicate aliquots of cDNA from each of these specimens were also run for PCR using primers for human G3PDH, and, in contrast to the reactions with human PSA primers, in which the sample lacking LNCaP cells failed to give a reaction product, all specimens yielded the expected 983 bp G3PDH DNA fragment (FIG. 2). All subsequent reactions on patient specimens were carried out so that each cDNA had a duplicate reaction containing G3PDH primers as a positive control for cDNA integrity. Each subsequent PCR experiment involving patient samples included one specimen of LNCaP cDNA to serve as a positive control reaction for PSA detection. In addition, a sample having no added cDNA was included among the specimen set to provide a negative control and to ensure against contamination of PCR reagents.

C. PCR analysis on Bloods From Control Patients

Figure 3A:
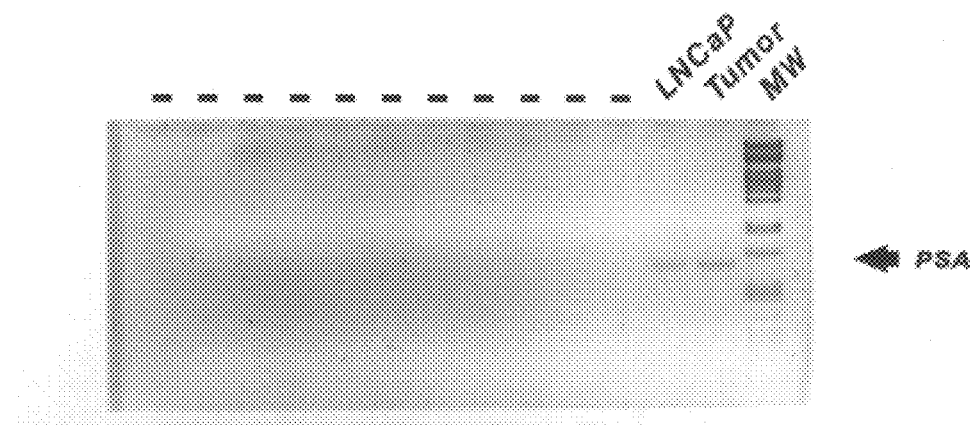
FIG. 3. Inability to detect PSA synthesizing cells in peripheral blood lymphocytes of noncancer male patients. Total RNA was extracted from the lymphocyte fraction of 8 young males with no history of urological disease and age-matched BPH patients. These RNAs were assayed by RT-PCR with PSA primers. None of these specimens yielded a positive fragment by ethidium bromide visualization (top panel) or by the enhanced visualization method (not shown). All specimens did yield an appropriate reaction product when G3PDH primers were utilized in the PCR reaction.
Figure 3B:
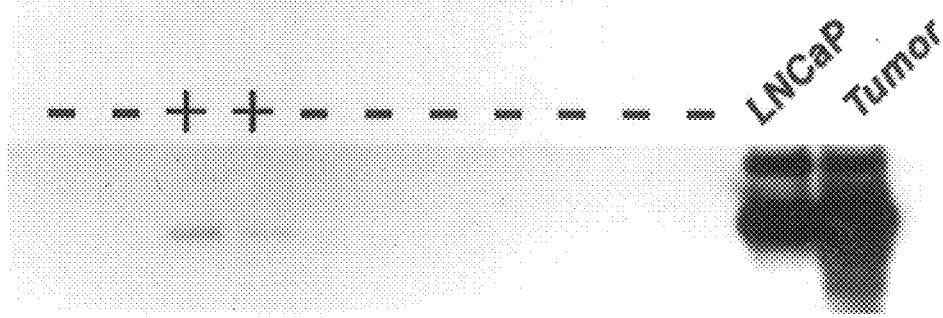

PCR analysis was performed on the RNA extracted from venous blood lymphocytes obtained from 20 male subjects (ages 19–41), and 20 female patients (ages 23–76). None of these control specimens revealed a positive PCR reaction (FIG. 3 and FIG. 4). In addition, lymphocyte fraction RNA of 25 age-matched BPH patients were analyzed to determine the possible effect of BPH on the PCR assay. None of these patients revealed a positive PCR fragment as assessed by ethidium bromide staining of the agarose gel following electrophoresis. The addition of digoxigenin-dUTP to the PCR reaction enabled us to increase the sensitivity of detection of the PSA-PCR fragment as described in more detail for our prostate cancer patients. The enhanced method of detection was performed on each of these groups of patients, and the 710 bp PSA DNA fragment was not detected in any specimen (not shown).

D. PCR analysis of Bloods from Metastatic Prostate Cancer Patients

Ten patients with confirmed but untreated metastatic prostate cancer were analyzed by the RT-PCR assay. All patients in this category had positive bone scans indicating the presence of bony metastases. PSA values for patients in this group ranged from 42 to 412 ng/ml. The peripheral lymphocyte RNA RT-PCR assay for 8 of these 10 patients revealed the presence of the 710 bp PSA PCR fragment. Five of these positives were revealed by ethidium bromide visualization and 3 additional specimens were revealed by the enhanced method for detection (not shown here).

E. PCR Analysis on Bloods from Localized Prostate Cancer Patients

Lymphocyte fraction RNAs from a total of 48 patients with clinically confined prostate cancer were analyzed by RT-PCR for PSA. Only 4 of these patients were positive for the PSA-PCR reaction by ethidium bromide staining analysis following agarose gel electrophoresis. However, an additional 7 patients were found to be positive with the use of the enhanced method of detection (FIG. 5, A and B), bringing the total to 11 (or 22.9% of patients in this category). The radical prostatectomy specimens obtained from these patients were subsequently analyzed as to the status of the Gleason grade of the tumor; whether the tumor extended into the prostatic capsule (capsular penetration); the presence of tumor at the surgical margins; and seminal vesicle involvement. None of these patients had detectable metastasis to the pelvic lymph nodes.

Table 1 summarizes the correlation of the patient PCR analysis with respect to pathological tumor stage. In the 48 patients operated for clinically localized prostate cancer, 15 (31.2%) were subsequently found to have tumor penetrating the prostatic capsule. Of these 15 patients, an RT-PCR fragment for PSA was amplified from 11 of the blood specimens. Therefore, if the RT-PCR blood assay was utilized as a means to discriminate prostate cancer patients with only capsular invasion from this population, it would have a sensitivity of 73% and a specificity of 89%. Ten of the 48 patients were subsequently found to have tumor present at the surgical margin (20.8% of surgical patient population). Nine of these 10 margin positive patients were also positive for PSA by RT_PCR> We calculated the sensitivity and specificity of the PCR assay for detecting margin positive disease in this patient population at 90% and 94%, respectively. Based on our statistical analysis, the RT-PCR assay is a

TABLE 1

Comparison of PCR findings in 48 patients with clinically localized prostate cancers and final pathological stage. Sensitivity, specificity, and predictive values were calculated for PCR in each category of pathology.

|  | POSITIVE MARGINS | CAPSULAR PENETRATION | POSITIVE SEMINAL VESICLE |
|---|---|---|---|
| Number of Patients PCR+ | 10/48 (20.8%) 9 | 15/48 (31.2%) 11 | 2/48 (4.16%) 1 |
| Sensitivity | 90% | 73% | 50% |
| Specificity | 94% | 89.2% | 75.6% |
| Positive Predictive Value | 82% | 78% | 78% |
| Negative Predictive Value | 93% | 61% | 18% | strong predictor of tumor spread through and beyond the prostatic capsule. An odds ration analysis of this 48 patient sample (patient group 2) estimating the likelihood that the presence of tumor at the surgical margin would be associated with a positive PCR assay was 162 (95% confidence limits: 13.1 to 1991.6), respectively. Finally, 2(4.16%) of the 48 surgical patients were found to have tumor invading the seminal vesicle. The PCR assay had a 50% sensitivity and 75.6% specificity for detecting patients with disease into the seminal vesicles. However, there were only 2 patients in the study with positive seminal vesicles, therefore, no good statistical correlation could be determined for this subgroup of patients. Used as an independent variable to predict prostate cancer confined to the prostate gland, RT-PCR for PSA had a positive predictive value of 81.8%.

The staging results predicted by preoperative imaging modalities were statistically compared to the results obtained with PCR. Prior to surgery, all patients had a serum PSA obtained and DRE by performed by one examiner (CAO). Patients either had a CT-scan of the pelvis, an endorectal coil MRI, or both to detect extraprostatic disease. Imaging sensitivity and specificity for disease confined to the prostate is listed in Table 2 and compared to the results of the RE-PCR assay. RT-PCR revealed the highest overall sensitivity for detecting extraporstatic tumor (73%).

Additionally, a stepwise logistic regression analysis was performed to identify the single variable (PSA, PSAD, CT scan, endorectal MRI or PCR) which would predict cancer at the surgical margin. The RT-PCR assay had the highest Chi-square score ($\chi^2=25.3$ p>0.0001) for this distinction (Table 2). In fact, RT-PCR proved to be the only variable which met a

TABLE 2

Comparison of PCR to standard pre-operative staging modalities in 48 patients undergoing radical prostatectomy. PCR was found to have the highest sensitivity and predictor of confined prostate cancer (negative predictive value).

|  | PCR | DRE | CT SCAN | ENDORECTAL COIL MRI |
|---|---|---|---|---|
| TRUE (+) | 11 | 2 | 2 | 1 |
| TRUE (−) | 32 | 37 | 28 | 3 |
| FALSE (+) | 0 | 0 | 5 | 1 |
| FALSE (−) | 5 | 9 | 6 | 3 |
| SENSITIVITY TP/TP + FN | 68.7% | 18% | 25% | 25% |
| SPECIFICITY TN/TN + FP | 100% | 100% | 84.8% | 75% | confidence level of 95%. Prostate specific antigen density (PSAD) is defined as a unitless ratio combining the value of the serum PSA measurement with the prostate volume. PSAD has been previously shown to be useful predictor for distinguishing benign from malignant prostate tissue (16). The mean PSAD was 0.29 in our surgical patient population with a standard deviation of 0.25. Table 3 compares the PSAD to the pathological stage for these patients. In this series, PSAD as a single predictor of margin positive disease was second best to RT-PCR. Stepwise logarithmic analysis of PSAD for this group of patients revealed a Chi-square score of 11.0, p>0.0009. Simple serum PSA values are compared to the final pathological stage in Table 4. The majority of patients (54%) had PSA values in the 4 to 10 ng/ml range. The mean PSA value for all patients was 11.2 ng/ml (S.D. +7.9). The Chi-square score for PSA as a single-modality predictor of extraprostatic disease was calculated to be $\chi^2=7.09$p>0.0001. Only 2 patients had PSA values greater than 30. Both of these patients were found to have positive surgical margins and were also PCR positive.

It is of further interest that 9 of the 48 radical prostatectomy patients had received flutamide therapy prior to their surgery and prior to the phlebotomy from which the PSA-PCR assay was performed. This subset of patients included 2 which had a positive PCR reaction and 7 which were negative. Cochran-Mantel-Haenszel summary odds ratio analysis controlling for patients given flutamide therapy resulted in an adjusted odds ration of 69.7 (95% confidence limits: 6.6 to 725.6). Furthermore, removal of these flutamide-treated patients from the rest of the surgical patients did not affect the strong correlation between positivity on the PCR assay and the presence of tumor at the surgical confined disease, it was positive only in a much smaller subset (22.9%) of these patients. Because the subset of patients detected by the PSA-PCR assay correlated strongly with local invasive spread of the cancer, the significance of this determination may lie in a more accurate measure of

TABLE 3

Correlation of PSAD and pathological stage in 48 patients with clinically localized cancer of the prostate.

| PSAD | NUMBER OF PATIENTS | +PCR | POSITIVE MARGINS | POSITIVE CAPSULE | POSITIVE SEMINAL VESICLE |
|---|---|---|---|---|---|
| 0–0.15 | 10 | 1(10%) | 1(10%) | 1(10%) | 0(0%) |
| 0.16–0.30 | 20 | 3(15%) | 2(10%) | 7(35%) | 0(0%) |
| 0.31–0.60 | 10 | 3(30%) | 2(20%) | 2(20%) | 1(10%) |
| >0.60 | 8 | 4(50%) | 5(63%) | 6(75%) | 1(12.5%) |
| TOTAL | 48(100%) | 11(22.9%) | 10(20.8%) | 15(31.2%) | 2(4.2%) |

TABLE 4

Correlation of serum PSA and pathological stage in 48 patients with clinically localized cancer of the prostate.

| PSA/(ng/ml) | NUMBER OF PATIENTS | +PCR | POSITIVE MARGINS | POSITIVE CAPSULE | POSITIVE SEMINAL VESICLE |
|---|---|---|---|---|---|
| 0–4.0 | 2 | 0(0%) | 0(0%) | 0(0%) | 0(0%) |
| 4.1–10.0 | 26 | 3(11.5%) | 3(11.5%) | 6(23%) | 0(0%) |
| 10.1–20 | 14 | 3(21.4%) | 3(21.4%) | 6(42.8%) | 0(0%) |
| 20.1–30 | 4 | 3(75%) | 2(50%) | 2(50%) | 2(50%) |
| 30.1–40 | 2 | 2(100%) | 2(100%) | 2(100%) | 0(0%) |
| Total | 48 | 11 | 10 | 16 | 2 | margin. With this change, the RT-PCR assay now had 100% sensitivity for identifying margin positive disease with a specificity of 93.5%.

III. Discussion

In this study, we have determined that the detection of blood-borne PSA-synthesizing cells by RT-PCR can be accomplished in patients with localized as well as metastatic prostate cancer and this detection provides a reliable marker for predicting local invasion of a prostate tumor prior to surgical procedures. PSA, a 34,000 kd glycoprotein, is a prostate-specific serine protease which is expressed exclusively by prostate epithelial cells, the cells most frequently involved in prostatic oncogenesis (17). In recent years, assays used to detect this protein in the blood have revolutionized the management of prostate cancer patients by allowing the earlier detection of prostate tumors as well as by providing a more effective means to follow the progression of the disease. As we have shown here, the specificity of PSA for prostate cells has further enabled the development of this RT-PCR based assay that can detect as few as 1 PSA-synthesizing cell in 100,000 blood cells. When this assay was applied to peripheral blood specimens taken from prostate cancer patients with confirmed metastases, it was positive for the overwhelming majority (80%) of patients in this category available for our study. The biological significance of these prostate cells in the circulation is not known at the present time. However, the high percentage of frank metastatic patients that give a positive reaction on this assay suggests that it is detecting circulating metastatic prostate cells. When this assay was applied to blood specimens taken from prostate cancer patients with suspected prostate-staging than with the imaging modalities utilized today (ie. MRI, bone scan and CT-scan). Statistical analysis of the data gathered in this survey supports the presumption that patients with localized prostate cancer that react positively on this assay represent a subset that are at increased risk for recurrent disease, despite surgical extirpation of the gland.

Two previous studies in the literature have addressed the concept of hematogenous dissemination of prostate cancer. Using flow cytometry, Hamdy et al. demonstrated that PSA-positive cells could be detected in 25 prostate cancer patients with bone metastasis while none of the control patients had PSA-positive cells in the peripheral blood (18). The results of this study were peculiar in the some patients had greater than 50% PSA-positive cells in the circulating lymphocyte fraction. However, a second report, describing the PCR amplification of a PSA DNA fragment from reverse transcribed peripheral blood RNA of metastatic prostate cancer patients confirmed its detection in 4 of 12 patients (33%) whereas it was never identified in a small group of control (non-cancer) patients (10). Our current investigation included 3 groups of non-cancer control patients and we never detected an appropriate PSA RT-PCR fragment from any blood specimen obtained from women, young males, or age-matched control males with benign enlargement of the prostate gland (total of 65 specimens). Therefore, as supported by the previous study (10) and by our current results, there is no evidence to date that non-prostate cancer patients have PSA-synthesizing cells present in the peripheral circulation. In contrast, untreated metastatic prostate cancer patients were overwhelmingly positive on this assay (80%). Moreover, the only other group that gave a positive reaction on this assay were a minority of patients (11 of 48 or 22.9%)

with suspected clinically localized prostate cancer. Therefore, our results indicate that the blood-based RT-PCR assay for PSA is specific for prostate cancer patients.

In our series of patients with localized prostate cancer, 10 patients were found to have tumor at the surgical margin subsequent to their radical surgery. Of these 10 patients, 9 had a positive RT-PCR reaction for PSA (90% sensitivity). Of the remaining 38 patients with margin negative disease, only 2 were found to have a positive PCR result (94% specificity). This is convincing evidence that a strong clinical correlation exists between the local extent of the tumor and hematogenous dissemination. In the patients with capsular penetration, the PCR assay was less sensitive than for margin positive disease (73%). Prostate cell dissemination into the circulation may therefore be a factor of the primary tumor volume. As tumor volume increases and encroaches on blood vessels, the basement membrane of endothelium may break down, allowing for tumor cells to enter the circulation. Interestingly, none of the patients in this group were found to have lymph node involvement, and all patients had negative bone scans, indicating that hematogenous dissemination may occur prior to lymphatic or bony involvement.

In this study, a fraction of the patients were given a course of flutamide therapy for "downstaging" of bulky tumors. Since 2 of these treated patients were positive on the PCR assay, it is clear that a short course of flutamide therapy does not abolish the ability of this PCR assay to detect circulating prostate cells. Considering that the only patient that had tumor at the surgical margin and remained unreactive on the assay was of this treatment group, allows for the possibility that flutamide treatment prior to phlebotomy may decrease the sensitivity of the PCR assay. However, the results of the Cochran-Mantel-Haenzszel summary odds ratio analysis controlling for flutamide-treated patients remained statistically significant, suggesting that flutamide does not meaningfully alter the sensitivity of the PSA-PCR assay.

The presence or absence of extracapsular prostate cancer is often the critical factor in therapeutic decisions regarding prostate cancer. Radical prostatectomy has been shown to be the most effective therapy when disease remains confined to the gland (19, 20). Microscopic disease that invades into the capsule or to the surgical margin significantly reduces the chance for cure. Several studies have shown that tumor can be detected at the surgical margin in 11 to 32% of clinical stage A patients and 23–71% of clinical stage B prostate cancer patients (21, 22). These high numbers directly reflect the inaccuracies of the current preoperative staging modalities. A recent report from a multi-institutional investigation comparing MRI and TRUS in the early staging of prostate cancer concluded that these modalities are not highly accurate because neither technique could identify microscopic spread (23). Eight patients in this current study had MRI with endorectal coils prior to surgery. This expensive modality was able to predict confined tumor in 50% of the cases. If the MRI was interpreted as positive, i.e. extracapsular, the MRI results were only 50% accurate. From a statistical standpoint, when PCR was compared to preoperative imaging, the PCR assay had the highest reliability (based on Chi-square analysis) in predicting margin positive disease.

The most common used imaging modality for local staging cancer is still the CT-scan, even though this modality traditionally understages a significant number of patients. From the perspective of prognostic ability and cost effectiveness perspective CT scanning is under serious investigation (24). Review of the CT-scan findings from our study do not contrast with those reported in other series (25,26). The CT-scan revealed a 25% sensitivity, and could accurately predict disease outside of the gland in only 28.5% of the cases.

Other studies in the literature have correlated the serum PSA and PSAD with extraprostatic involvement and lymph node metastasis (27, 28, 29, 30). In the 48 patients with localized prostate cancer, the PSAD for patients with positive and negative results on RT-PCR was 0.47 and 0.25 respectively. Recent investigations have demonstrated that a PSAD value greater than 0.3 is associated with a high incidence of extraprostatic disease (31). Our findings of PSA-synthesizing cells in the peripheral circulation of patients circulation of patients with localized prostate cancer and this high PSAD are consistent with this hypothesis.

To our knowledge, this is also the first report employing digoxigenin-labeling as a detection system to enhance the PCR reaction. This enhanced method of detection enabled us to detect an additional 7 patients with localized prostate cancer that would have been missed by conventional ethidium-bromide staining of the agarose gel. We also performed the enhanced detection on all control patient reactions to ensure that these were negative by both techniques, and found that all controls proved negative.

The possibility of staging prostate cancer patients with a 5 cc sample of peripheral blood has several important implications. The future use of such a PCR-based assay has the potential for significantly decreasing the total cost of prostate cancer management. Since this assay appears to be more accurate than current screening modalities, it may enable a reduction not only in the number of preoperative CT-scans and MRI's, but also in the number of radical cancer operations performed. The social and ethical considerations extend to the patient with prostate cancer who may be spared the morbidity of an operation that would otherwise be indicated. And finally, our ability to predict the cure rate in patients undergoing radical cancer surgery will be greatly enhanced with this highly sensitive, accurate test.

REFERENCES

1. Lu-Yao, G., Mclerran, D., Wasson, J., and Wennberg, J. An assessment of radical prostatectomy. J.A.M.A. 269:2633–2655 (1993).
2. Epstein, J., Pizov, G., and Walsh, P. C. correlation of pathologic findings after radical retropubic prostatectomy. Cancer 71:3582–3593 (1993).
3. Epstein, J., Carmichael, M., Pizov, G., and Walsh, P. C. Influence of capsular penetration on progression following radical prostatectomy: A study of 196 cases with long-term follow-up. J. Urol. 150:135–141 (1993).
4. McNeal, J., Villers, A., Redwine, E. A., Freiha, F. S. and Stamey, T. A. Capsular penetration in prostate cancer: Significance for natural history and treatment. Amer. J. Surg. Path. 14:240–247 (1990).
5. Anscher, M. S. and Prosnitz. Postoperative radiotherapy for patients with carcinoma of the prostate undergoing radical prostatectomy with positive surgical margins, seminal vesicle involvement and/or penetration through the capsule. J. Urol. 138:1407–1412 (1987).
6. Voges, G. E., McNeal, J. E., Redwine, E. A., Freiha, F. S. and Stamey, T. S. Morphologic analysis of surgical margins with positive findings in prostatectomy for adenocarcinoma of the prostate. Cancer 69 :520–526 (1992).
7. Catalona, W. J., Dresner, S. M. Nerve-sparing radical prostatectomy: Extraprostatic tumor extension and preservation of erectile function. J. Urol. 134:1149–1151 (1985).

8. Batson, O. V. The function of the vertebral veins and their role in the spread of metastasis. *Ann. Surg.* 112:138–142 (1940).
9. Dodds, P. R., Caride, V. J., and Lytton, B. The role of the vertebral veins in the dissemination of prostate cancer. *J. Urol.* 126:753–755 (1981).
10. Moreno, J. G., Croce, C. M., Fischer, R., Monne, M., Vihko, P., Mulholland, S. G. and Gomella, L. G. Detection of hematogenous micrometastasis in patients with prostate cancer. *Can. Res.* 52:6110–6112 (1992).
11. Horoszewicz, J. S., Leung, S. S., Kawinski, E., Karr, J. P., Rosenthal, H., Chu, T. M., Mirand, E. A>, and Murphy, G. P. LnCaP model of human prostatic carcinoma. *Can. Res.* 43:1809–1817 (1983).
12. Chomezynski, P., and Sacchi, N. Single-step method of RNA isolation by acid guanidinium thiocyanate-phenol-chloroform extraction. *Annal. Biochem.* 162:156–159 (1987).
13. Sanger, F., Nicklen, S., and Coulson, A. R. DNA sequencing with chain-terminating inhibitors. *Proc. Natl. Acad. Sci. USA* 74:5463–5467 (1977).
14. Klobeck, H. G., Combriato, G., Schultz, P., Arbusow, V. and Fittler, F. Genomic sequences of human prostate specific antigen (PSA). *Nucleic Acids Res.* 17:3981–3989 (1989).
15. Sambrook, J., Fritsch, E. F., and Maniatis, T. Molecular Cloning: A Laboratory Manual, Second Edition, (Cold Spring Harbor, N.Y.: Cold Springs Harbor Press) (1989).
16. Benson, M. C., Whang, I. S., Pantuk, A., Ring, K., Kaplan, S. A., Olsson, C. A. and Cooner, W. H. Prostate Specific Antigen Density: A means of distinguishing benign prostatic hypertrophy and prostate cancer. *J. Urol.* 147:815–816 (1992).
17. Wang, M. C., Valenzuela, L. A., Murphy, G. P. and Chu, T. M. Purification of a human prostate specific antigen. *Invest. Urol.* 17:159–164 (1979).
18. Hamdy, F. C., Lawry, J., Anderson, J. B., Parsons, M. S., Rees, R. C. and Williams, J. L. 1992. Circulating prostate specific antigen-positive cells correlate with metastatic prostate cancer. *Brit. J. Urol.* 69:392–396 (1979).
19. Walsh, P. C. Radical prostatectomy for the treatment of localized prostate cancer. *Urol. Clin. N. Amer.* 7:583–594 (1980).
20. Jewett, H. J., Bridge, H. W., Gray, G. F., and Shelly, W. M. The palpable nodule of prostate cancer. Results of 15 years after radical excision. *J.A.M.A.* 203:403-144 (1968).
21. Mukamel, E., Hanna, J., and deKernion, J. B. Staging errors in clinically localized prostate cancer. *Urol.* 30:318–323 (1982).
22. Rosen, M. A., Goldstone, L. Lapin, S., Wheeler, T., and Scardino, P. Frequency and location of extracapsular extension and positive surgical margins in radical prostatectomy specimens. *J. Urol.* 148:331–337 (1192).
23. Rifkin, M. D., Zerhouni, E. A., Gatsonis, C. A., Quint, L. E., Paushter, D. M. et al. Comparison of magnetic resonance imaging and ultrasonography in staging early prostate cancer. *New Eng. J. Med.* 323:621–626 (1990).
24. Platt, J. F., Bree, R. L. and Schwab, R. E. The accuracy of CT in the staging of the prostate. *Amer. J. Roent.* 149:315–318 (1987).
25. Salo, J. O., Kivisaari, L., Rannikko, S. and Lehtonen, T. Computerized tomography and transrectal ultrasound in the assessment of local extension of prostatic carcinoma before radical retropubic prostatectomy. *J. Urol.* 137:435–438 (1987).
26. Hricak, H., et al. Prostatic carcinoma: Staging by clinical assessment, CT, and MR imaging. *Radiology* 162:331–335 (1987).
27. Oesterling, J., Martin, S., Bergstralh, E. and Lowe, F. C. The use of prostate specific antigen in staging patients with newly diagnosed prostate cancer. *J.A.M.A* 269:57–60 (1993).
28. Winter, H. I., Bretton, P. R. and Herr, H. W. Preoperative prostate-specific antigen in predicting pathological stage and grade after radical prostatectomy. *Urology* 38:202–205 (1991).
29. Hudson, M. A., Bahnson, R. R., and Catalona, W. J. Clinical use of prostate specific antigen density in patients with prostate cancer. *J. Urol.* 142:1011–1017 (1989).
30. Gerber, G. S., and Goldberg, R., and Chodak, G. W. Local staging of prostate cancer by tumor volume, prostate-specific antigen, and transrectal ultrasound. *Urology* 40:311–316 (1992).
31. Seaman, E., Kistler, S., Katz, A. E. and Benson, M. C. The use of PSAD to predict D-0 prostatic carcinoma. *J. Urol.* 149:300A (1993).

What is claimed is:

1. A method for enhancing the detection of prostate specific antigen in a biological sample suspected of containing prostate specific antigen which comprises:

(a) extracting mRNA from the sample;

(b) contacting the mRNA from step (a) with reverse transcriptase under conditions allowing for the production of cDNA;

(c) contacting the cDNA from step (b) with a pair of reverse transcriptase polymerase chain reaction oligonucleotide primers capable of specifically hybridizing with DNA encoding prostate specific antigen, wherein one such primer is an oligonucleotide 12 to 30 nucleotides in length, comprising the sequence 5'-X-CACCCCATCCTA-Y-3' and the second such primer is an oligonucleotide 12 to 30 nucleotides in length and having the nucleotide sequence 5'-X'-TCCAGCCACGAC-Y'-3' wherein each of X, X', Y, and Y' may be present or absent, but if present X is A, GA, AGA, CAGA, ACAGA, CACAGA, ACACAGA, AACACAGA, TAACACAGA, ATAACACAGA, AATAACACAGA, AAATAACACAGA, or CAAATAACACAGA; X' is C, AC, GAC, TGAC, ATGAC, GATGAC, TGATGAC, GTGATGAC, GGTGATGAC, AGGTGATGAC or CAGGTGATGAC; Y is T, TC, TCT, TCTG, TCTGT, or TCTGTG; and Y' is C, CT, CTC, CTCA, CTCAT, CTCATG, or CTCATGC; and wherein at least one of the primers is covalently linked to a suitably modified digoxigenin molecule, under conditions allowing for hybridization of both primers to any cDNA encoding prostate specific antigen so as to obtain a double stranded duplex comprising the cDNA hybridized to the primers;

(d) contacting the double stranded duplex from step (c) with DNA polymerase under conditions allowing for the extension of the primers to produce cDNA encoding prostate specific antigen and comprising a suitably modified digoxigenin molecule; and (e) detecting the suitably modified digoxigenin molecule from the cDNA from step (d) thereby detecting prostate specific antigen.

2. The method of claim 1, wherein in step (c) the first primer is 5'-CACAGACACCCCATCCTATC-3' SEQ ID NO: 3 and the second primer is 5'-GATGACTCCAGCCACGACCT-3' SEQ ID NO: 4.

3. The method of claim 1, wherein in step (e) detection is accomplished using a detectably labeled antibody which specifically binds to the suitably modified digoxigenin molecule.

4. The method of claim 3, wherein the detectably labeled antibody is labeled with an enzyme.

5. The method of claim 4, wherein the enzyme is alkaline phosphatase.

6. The method of claim 1, wherein the biological sample is a sample from the peripheral blood of a subject.

7. The method of claim 1, wherein the biological sample is a sample from the lymph nodes of a subject.

8. A method for detecting prostate specific antigen in a biological sample suspected of containing prostate specific antigen which comprises:

(a) extracting mRNA from the sample;

(b) contacting the mRNA from step (a) with reverse transcriptase under conditions allowing for the production of cDNA;

(c) contacting the cDNA from step (b) with a pair of reverse transcriptase polymerase chain reaction oligonucleotide primers capable of specifically hybridizing with DNA encoding prostate specific antigen, wherein one such primer is an oligonucleotide 12 to 30 nucleotides in length and having the sequence 5'-X-CACCCCATCCTA-Y-3' and the second such primer is an oligonucleotide 12 to 30 nucleotides in length, comprising the nucleotide sequence 5'-X'-TCCAGCCACGAC-Y'-3' wherein each of X, X', Y, and Y' may be present or absent, but if present X is A, GA, AGA, CAGA, ACAGA, CACAGA, ACACAGA, AACACAGA, TAACACAGA, ATAACACAGA, AATAACACAGA, AAATAACACAGA, or CAAATAACACAGA; X' is C, AC, GAC, TGAC, ATGAC, GATGAC, TGATGAC, GTGATGAC, GGTGATGAC, AGGTGATGAC or CAGGTGAT-GAC; Y is T, TC, TCT, TCTG, TCTGT, or TCTGTG; and Y' is C, CT, CTC, CTCA, CTCAT, CTCATG, or CTCATGC; under conditions allowing for hybridization of both primers to any cDNA encoding prostate specific antigen so as to obtain a double stranded duplex comprising the cDNA hybridized to the primers;

(d) contacting the double stranded duplex from step (c) with DNA polymerase under conditions allowing for the extension of the primers to produce cDNA encoding prostate specific antigen; and (e) detecting the cDNA from step (d) thereby detecting prostate specific antigen.

9. The method of claim 8, wherein in step (c) the first primer is 5'-CACAGACACCCCATCCTATC-3' and the second primer is 5'-GATGACTCCAGCCACGACCT-3'.

10. The method of claim 8, wherein the biological sample is a sample from the peripheral blood of a subject.

11. The method of claim 8, wherein the biological sample is a sample from the lymph nodes of a subject.

12. A method of diagnosing prostate cancer in a subject which comprises:

(a) obtaining a biological sample from the subject;
(b) extracting mRNA from the sample;
(c) contacting the mRNA from (b) with reverse transcriptase under conditions allowing for the production of cDNA;
(d) contacting the cDNA from step (c) with a pair of reverse transcriptase polymerase chain reaction oligonucleotide primers capable of specifically hybridizing with DNA encoding prostate specific antigen, wherein one such primer is an oligonucleotide 12 to 30 nucleotides in length, comprising the sequence 5'-X-CACCCCATCCTA-Y-3' and the second such primer is an oligonucleotide 12 to 30 nucleotides in length and having the nucleotide sequence 5,' -X -TCCAGCCACGAC-Y' -3' wherein each of X, X', Y, and Y' may be present or absent, but if present X is A, GA, AGA, CAGA, ACAGA, CACAGA, ACACAGA, AACACAGA, TAACACAGA, ATAACACAGA, AATAACACAGA, AAATAACACAGA, or CAAATAACACAGA; X' is C, AC, GAC, TGAC, ATGAC, GATGAC, TGATGAC, GTGATGAC, GGTGATGAC, AGGTGATGAC or CAGGTGAT-GAC; Y is T, TC, TCT, TCTG, TCTGT, or TCTGTG; and Y' is C, CT, CTC, CTCA, CTCAT, CTCATG, or CTCATGC; under conditions allowing for hybridization of both primers to any cDNA encoding prostate specific antigen so as to obtain a double stranded duplex comprising the cDNA hybridized to the primers;
(e) contacting the double stranded duplex from step (d) with DNA polymerase under conditions allowing for the extension of the primers to produce DNA encoding prostate specific antigen; and
(f) detecting the DNA from step (e) thereby diagnosing prostate cancer in the subject.

13. The method of claim 12, wherein in step (c) the first primer is 5'-CACAGACACCCCATCCTATC-3' SEQ ID NO: 3 and the second primer is 5'-GATGACTCCAGCCACGACCT-3' SEQ ID NO: 4.

14. The method of claim 12, wherein at least one of the primers in the set of reverse transcriptase polymerase chain reaction primers is covalently linked to a suitably modified digoxigenin molecule.

15. The method of claim 14, wherein the detection of DNA in step (f) comprises detection of the suitably modified digoxigenin molecule with a detectably labeled antibody which specifically binds to the suitably modified digoxigenin molecule.

16. The method of claim 15, wherein the detectably labeled antibody is labeled with an enzyme.

17. The method of claim 16, wherein the enzyme is alkaline phosphatase.

18. The method of claim 12, wherein the biological sample is a sample from the peripheral blood of a subject.

19. The method of claim 12, wherein the biological sample is a sample from the lymph nodes of a subject.

20. A method of determining the stage of prostate cancer in a subject which comprises:

(a) obtaining a biological sample from the subject;
(b) extracting mRNA from the sample;
(c) contacting the mRNA from (b) with reverse transcriptase under conditions allowing for the production of cDNA;
(d) contacting the cDNA from step (c) with a pair of reverse transcriptase polymerase chain reaction oligonucleotide primers capable of specifically hybridizing with DNA encoding prostate specific antigen, wherein one such primer is an oligonucleotide 12 to 30 nucleotides in length and having the sequence 5'-X-CACCCCATCCTA-Y-3' and the second such primer is an oligonucleotide 12 to 30 nucleotides in length, comprising the nucleotide sequence 5'-X'-TCCAGCCACGAC-Y'-3' wherein each of X, X', Y, and Y' may be present or absent, but if present X is A, GA, AGA, CAGA, ACAGA, CACAGA, ACACAGA, AACACAGA,. TAACACAGA, ATAACACAGA, AATAACACAGA, AAATAACACAGA, or CAAATAACACAGA; X' is C, AC, GAC, TGAC, ATGAC, GATGAC, TGATGAC, GTGATGAC, GGTGATGAC, AGGTGATGAC or CAGGTGAT-GAC; Y is T, TC, TCT, TCTG, TCTGT, or TCTGTG; and Y' is C, CT, CTC, CTCA, CTCAT, CTCATG, or CTCATGC; under conditions allowing for hybridization of both primers to any cDNA encoding prostate specific antigen so as to obtain a double stranded duplex comprising the cDNA hybridized to the primers;
(e) contacting the double stranded duplex from step (d) with DNA polymerase under conditions allowing for the extension of the primers to produce DNA encoding prostate specific antigen; and
(f) detecting the DNA from step (e) thereby determining the stage of prostate cancer in the subject.

21. The method of claim 20, wherein in step (d) the first primer is 5'-CACAGACACCCCATCCTATC-3' SEQ ID NO: 3 and the second primer is 5'-GATGACTCCAGCCACGACCT-3' SEQ ID NO: 4.

22. The method of claim 20, wherein at least one of the primers in the pair of reverse transcriptase polymerase chain reaction oligonucleotide primers is covalently linked to a suitably modified digoxigenin molecule.

23. The method of claim 22, wherein the detection of DNA in step (f) comprises detection of the suitably modified digoxigenin molecule with a detectably labeled antibody which specifically binds to the suitably modified digoxigenin molecule.

24. The method of claim 23, wherein the detectably labeled antibody is labeled with an enzyme.

25. The method of claim 23, wherein the enzyme is alkaline phosphatase.

26. The method of claim 20, wherein the biological sample is a sample from the peripheral blood of a subject.

27. The method of claim 20, wherein the biological sample is a sample from the lymph nodes of a subject.

28. An oligonucleotide 12 to 30 nucleotides in length, comprising the sequence 5'-X-CACCCCATCCTA-Y-3' wherein each of X and Y may be present or absent, but if present X is A, GA, AGA, CAGA, ACAGA, CACAGA, ACACAGA, AACACAGA, TAACACAGA, ATAACACAGA, AATAACACAGA, AAATAACACAGA, or CAAATAACACAGA; and Y is T, TC, TCT, TCTG, TCTGT, or TCTGTG.

29. The oligonucleotide of claim 28 having the nucleotide sequence 5'-CACAGACACCCCATCCTATC-3' SEQ ID NO: 3.

30. The oligonucleotide of claim 28 or 29 covalently linked to a suitably modified digoxigenin molecule.

31. An oligonucleotide 12 to 30 nucleotides in length and having the nucleotide sequence 5'-X'-TCCAGCCACGAC-Y'-3' wherein each of X' and Y' may be present or absent, but if present X' is C, AC, GAC, TGAC, ATGAC, GATGAC, TGATGAC, GTGATGAC, GGTGATGAC, AGGTGAT-GAC or CAGGTGATGAC; and Y' is C, CT, CTC, CTCA, CTCAT, CTCATG, or CTCATGC.

32. The oligonucleotide of claim 31 having the nucleotide sequence 5'-GATGACTCCAGCCACGACCT-3' SEQ ID NO: 4.

33. The oligonucleotide of claim 31 or 32 covalently linked to a suitably modified digoxigenin molecule.

34. A pair of reverse transcriptase polymerase chain reaction oligonucleotide primers for detecting the expression of the prostate specific antigen, wherein one such primer is an oligonucleotide 12 to 30 nucleotides in length, comprising the sequence 5'-X-CACCCCATCCTA-Y-3' and the second such primer is an oligonucleotide 12 to 30 nucleotides in length and having the nucleotide sequence 5'-X'-TCCAGCCACGAC-Y'-3' wherein each of X, X', Y, and Y' may be present or absent, but if present X is A, GA, AGA, CAGA, ACAGA, CACAGA, ACACAGA, AACACAGA, TAACACAGA, ATAACACAGA, AATAACACAGA, AAATAACACAGA, or CAAATAA-CACAGA; X' is C, AC, GAC, TGAC, ATGAC, GATGAC, TGATGAC, GTGATGAC, GGTGATGAC, AGGTGAT-GAC or CAGGTGATGAC; Y is T, TC, TCT, TCTG, TCTGT, or TCTGTG; and Y' is C, CT, CTC, CTCA, CTCAT, CTCATG, or CTCATGC.

35. The pair of reverse transcriptase polymerase chain reaction oligonucleotide primers of claim 34, wherein the first such primer is 5'-CACAGACACCCCATCCTATC-3' SEQ ID NO: 3 and the second such primer is 5'-GATGACTCCAGCCACGACCT-3'.

36. The pair of reverse transcriptase polymerase chain reaction oligonucleotide primers of claim 34 or 35, wherein at least one of the primers is covalently linked to a suitably modified digoxigenin molecule.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 1729 base pairs
      (B) TYPE: nucleic acid
      (C) STRANDEDNESS: single
      (D) TOPOLOGY: linear (ii) MOLECULE TYPE: cDNA (vi) ORIGINAL SOURCE:
      (A) ORGANISM: Homo sapiens (ix) FEATURE:
      (A) NAME/KEY: CDS
      (B) LOCATION: 378..1088

(xi) SEQUENCE DESCRIPTION: SEQ ID NO:1:

```
AAGTTTCCCT TCTCCCAGTC CAAGACCCCA AATCACCACA AAGGACCCAA TCCCCAGACT     60

CAAGATATGG TCTGGGCGCT GTCTTGTGTC TCCTACCCTG ATCCCTGGGT TCAACTCTGC    120

TCCCAGAGCA TGAAGCCTCT CCACCAGCAC CAGCCACCAA CCTGCAAACC TAGGGAAGAT    180

TGACAGAATT CCCAGCCTTT CCCAGCTCCC CCTGCCCATG TCCCAGGACT CCCAGCCTTG    240

GTTCTCTGCC CCCGTGTCTT TTCAAACCCA CATCCTAAAT CCATCTCCTA TCCGAGTCCC    300

CCAGTTCCTC CTGTCAACCC TGATTCCCCT GATCTAGCAC CCCCTCTGCA GGTGCTGCAC    360

CCCTCATCCT GTCTCGG ATT GTG GGA GGC TGG GAG TGC GAG AAG CAT TCC      410
                   Ile Val Gly Gly Trp Glu Cys Glu Lys His Ser
                    1               5                  10

CAA CCC TGG CAG GTG CTT GTA GCC TCT CGT GGC AGG GCA GTC TGC GGC     458
Gln Pro Trp Gln Val Leu Val Ala Ser Arg Gly Arg Ala Val Cys Gly
            15                  20                  25

GGT GTT CTG GTG CAC CCC CAG TGG GTC CTC ACA GCT ACC CAC TGC ATC     506
Gly Val Leu Val His Pro Gln Trp Val Leu Thr Ala Thr His Cys Ile
 30                  35                  40

AGG AAC AAA AGC GTG ATC TTG CTG GGT CGG CAC AGC CTG TTT CAT CCT     554
Arg Asn Lys Ser Val Ile Leu Leu Gly Arg His Ser Leu Phe His Pro
        45                  50                  55

GAA GAC ACA GGC CAG GTA TTT CAG GTC AGC CAC AGC TTC CCA CAC CCG     602
Glu Asp Thr Gly Gln Val Phe Gln Val Ser His Ser Phe Pro His Pro
 60                  65                  70                  75

CTC TAC GAT ATG AGC CTC CTG AAG AAT CGA TTC CTC AGG CCA GGT GAT     650
Leu Tyr Asp Met Ser Leu Leu Lys Asn Arg Phe Leu Arg Pro Gly Asp
                80                  85                  90

GAC TCC AGC CAC GAC CTC ATG CTG CTC CGC CTG TCA GAG CCT GCC GAG     698
Asp Ser Ser His Asp Leu Met Leu Leu Arg Leu Ser Glu Pro Ala Glu
                95                 100                 105

CTC ACG GAT GCT ATG AAG GTC ATG GAC CTG CCC ACC CAG GAG CCA GCA     746
Leu Thr Asp Ala Met Lys Val Met Asp Leu Pro Thr Gln Glu Pro Ala
            110                 115                 120

CTG GGG ACC ACC TGC TAC GCC TCA GGC TGG GGC AGC ATT GAA CCA GAG     794
Leu Gly Thr Thr Cys Tyr Ala Ser Gly Trp Gly Ser Ile Glu Pro Glu
125                 130                 135

GAG TTC TTG ACC CCA AAG AAA CTT CAG TGT GTG GAC CTC CAT GTT ATT     842
Glu Phe Leu Thr Pro Lys Lys Leu Gln Cys Val Asp Leu His Val Ile
140                 145                 150                 155

TCC AAT GAC GTG TGT GCG CAA GTT CAC CCT CAG AAG GTG ACC AAG TTC     890
Ser Asn Asp Val Cys Ala Gln Val His Pro Gln Lys Val Thr Lys Phe
                160                 165                 170

ATG CTG TGT GCT GGA CGC TGG ACA GGG GGC AAA AGC ACC TGC TCG GGT     938
Met Leu Cys Ala Gly Arg Trp Thr Gly Gly Lys Ser Thr Cys Ser Gly
            175                 180                 185

GAT TCT GGG GGC CCA CTT GTC TGT AAT GGT GTG CTT CAA GGT ATC ACG     986
Asp Ser Gly Gly Pro Leu Val Cys Asn Gly Val Leu Gln Gly Ile Thr
        190                 195                 200

TCA TGG GGC AGT GAA CCA TGT GCC CTG CCC GAA AGG CCT TCC CTG TAC    1034
Ser Trp Gly Ser Glu Pro Cys Ala Leu Pro Glu Arg Pro Ser Leu Tyr
205                 210                 215

ACC AAG GTG GTG CAT TAC CGG AAG TGG ATC AAG GAC ACC ATC GTG GCC    1082
Thr Lys Val Val His Tyr Arg Lys Trp Ile Lys Asp Thr Ile Val Ala
220                 225                 230                 235

AAC CCC TGAGCACCCC TATCAACTCC CTATTGTAGT AAACTTGGAA CCTTGGAAAT    1138
Asn Pro

GACCAGGCCA AGACTCAGGC CTCCCCAGTT CTACTGACCT TTGTCCTTAG GTGTGAGGTC    1198

CAGGGTTGCT AGGAAAAGAA ATCAGCAGAC ACAGGTGTAG ACCAGAGTGT TTCTTAAATG    1258
```

```
GTGTAATTTT GTCCTCTCTG TGTCCTGGGG AATACTGGCC ATGCCTGGAG ACATATCACT   1318

CAATTTCTCT GAGGACACAG ATAGGATGGG GTGTCTGTGT TATTTGTGGG GTACAGAGAT   1378

GAAAGAGGGG TGGGATCCAC ACTGAGAGAG TGGAGAGTGA CATGTGCTGG ACACTGTCCA   1438

TGAAGCACTG AGCAGAAGCT GGAGGCACAA CGCACCAGAC ACTCACAGCA AGGATGGAGC   1498

TGAAAACATA ACCCACTCTG TCCTGGAGGC ACTGGGAAGC CTAGAGAAGG CTGTGAACCA   1558

AGGAGGGAGG GTCTTCCTTT GGCATGGGAT GGGGATGAAG TAAGGAGAGG GACTGACCCC   1618

CTGGAAGCTG ATTCACTATG GGGGGAGGTG TATTGAAGTC CTCCAGACAA CCCTCAGATT   1678

TGATGATTTC CTAGTAGAAC TCACAGAAAT AAAGAGCTGT TATACTGTGA A            1729
```

(2) INFORMATION FOR SEQ ID NO:2:

(i) SEQUENCE CHARACTERISTICS:
        (A) LENGTH: 237 amino acids
        (B) TYPE: amino acid
        (D) TOPOLOGY: linear (ii) MOLECULE TYPE: protein (xi) SEQUENCE DESCRIPTION: SEQ ID NO:2:

```
Ile Val Gly Gly Trp Glu Cys Glu Lys His Ser Gln Pro Trp Gln Val
 1               5                  10                  15

Leu Val Ala Ser Arg Gly Arg Ala Val Cys Gly Gly Val Leu Val His
                20                  25                  30

Pro Gln Trp Val Leu Thr Ala Thr His Cys Ile Arg Asn Lys Ser Val
                35                  40                  45

Ile Leu Leu Gly Arg His Ser Leu Phe His Pro Glu Asp Thr Gly Gln
 50                  55                  60

Val Phe Gln Val Ser His Ser Phe Pro His Pro Leu Tyr Asp Met Ser
 65                  70                  75                  80

Leu Leu Lys Asn Arg Phe Leu Arg Pro Gly Asp Asp Ser Ser His Asp
                85                  90                  95

Leu Met Leu Leu Arg Leu Ser Glu Pro Ala Glu Leu Thr Asp Ala Met
                100                 105                 110

Lys Val Met Asp Leu Pro Thr Gln Glu Pro Ala Leu Gly Thr Thr Cys
                115                 120                 125

Tyr Ala Ser Gly Trp Gly Ser Ile Glu Pro Glu Glu Phe Leu Thr Pro
130                 135                 140

Lys Lys Leu Gln Cys Val Asp Leu His Val Ile Ser Asn Asp Val Cys
145                 150                 155                 160

Ala Gln Val His Pro Gln Lys Val Thr Lys Phe Met Leu Cys Ala Gly
                165                 170                 175

Arg Trp Thr Gly Gly Lys Ser Thr Cys Ser Gly Asp Ser Gly Gly Pro
                180                 185                 190

Leu Val Cys Asn Gly Val Leu Gln Gly Ile Thr Ser Trp Gly Ser Glu
                195                 200                 205

Pro Cys Ala Leu Pro Glu Arg Pro Ser Leu Tyr Thr Lys Val Val His
                210                 215                 220

Tyr Arg Lys Trp Ile Lys Asp Thr Ile Val Ala Asn Pro
225                 230                 235
```

(2) INFORMATION FOR SEQ ID NO:3:

(i) SEQUENCE CHARACTERISTICS:
        (A) LENGTH: 20 base pairs
        (B) TYPE: nucleic acid (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:3:

CACAGACACC CCATCCTATC                                                  20

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:4:

GATGACTCCA GCCACGACCT                                                  20